(12) United States Patent
Jalan et al.

(10) Patent No.: US 10,525,029 B2
(45) Date of Patent: *Jan. 7, 2020

(54) TREATMENT OF DISEASES ASSOCIATED WITH HEPATIC STELLATE CELL ACTIVATION USING AMMONIA-LOWERING THERAPIES

(71) Applicant: UCL Business PLC, London (GB)

(72) Inventors: Rajiv Jalan, London (GB); Rajeshwar Prosad Mookerjee, London (GB); Krista Rombouts, London (GB); Fausto Andreola, London (GB); Francesco De Chiara, London (GB); Karen Louise Thomsen, London (GB)

(73) Assignee: UCL BUSINESS LTD, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/026,403

(22) Filed: Jul. 3, 2018

(65) Prior Publication Data

US 2019/0070142 A1 Mar. 7, 2019

Related U.S. Application Data

(63) Continuation of application No. 15/527,999, filed as application No. PCT/US2015/062223 on Nov. 23, 2015, now Pat. No. 10,039,735.

(60) Provisional application No. 62/083,814, filed on Nov. 24, 2014.

(51) Int. Cl.
| | |
|---|---|
| *A61K 31/216* | (2006.01) |
| *A61K 31/192* | (2006.01) |
| *A61K 31/198* | (2006.01) |
| *A61K 31/437* | (2006.01) |
| *A61K 31/7004* | (2006.01) |
| *A61K 31/7016* | (2006.01) |
| *A61K 33/42* | (2006.01) |
| *A61K 9/00* | (2006.01) |
| *A61K 45/06* | (2006.01) |

(52) U.S. Cl.
CPC .......... *A61K 31/216* (2013.01); *A61K 9/0019* (2013.01); *A61K 9/0053* (2013.01); *A61K 31/192* (2013.01); *A61K 31/198* (2013.01); *A61K 31/437* (2013.01); *A61K 31/7004* (2013.01); *A61K 31/7016* (2013.01); *A61K 33/42* (2013.01); *A61K 45/06* (2013.01)

(58) Field of Classification Search
None
See application file for complete search history.

(56) References Cited

U.S. PATENT DOCUMENTS

| 3,950,529 A | 4/1976 | Fischer et al. |
|---|---|---|
| 4,100,293 A | 7/1978 | Walser |
| 4,228,099 A | 10/1980 | Walser |
| 4,284,647 A | 8/1981 | Brusilow et al. |
| 4,320,146 A | 3/1982 | Walser |
| 4,352,814 A | 10/1982 | Walser |
| 4,457,942 A | 7/1984 | Brusilow et al. |
| 5,139,981 A | 8/1992 | Kurland |
| 5,405,761 A | 4/1995 | Makryaleas et al. |
| 5,571,783 A | 11/1996 | Montagne et al. |
| 5,591,613 A | 1/1997 | Makryaleas et al. |
| 5,741,524 A | 4/1998 | Staniforth et al. |
| 5,767,086 A | 6/1998 | Kauvar et al. |
| 6,083,953 A | 7/2000 | Nestor et al. |
| 6,258,849 B1 | 7/2001 | Burzynski |
| 6,451,340 B1 | 9/2002 | Arimilli et al. |
| 6,503,530 B1 | 1/2003 | Kang et al. |
| 6,514,953 B1 | 2/2003 | Armitage et al. |
| 6,768,024 B1 | 7/2004 | Watson-Straughan et al. |
| 6,943,192 B2 | 9/2005 | Burzynski |
| 8,173,706 B2 | 5/2012 | Anderson et al. |
| 8,389,576 B2 | 3/2013 | Jalan et al. |
| 8,492,439 B2 | 7/2013 | Anderson et al. |
| 8,785,498 B2 | 7/2014 | Anderson et al. |
| 8,946,473 B2 | 2/2015 | Anderson et al. |
| 9,034,925 B2 | 5/2015 | Anderson et al. |
| 9,260,379 B2 | 2/2016 | Anderson et al. |
| 9,566,257 B2 | 2/2017 | Jalan et al. |
| 9,604,909 B2 | 3/2017 | Anderson et al. |
| 10,039,735 B2 | 8/2018 | Jalan et al. |
| 2003/0105104 A1 | 6/2003 | Burzynski |
| 2003/0195255 A1 | 10/2003 | Summar |
| 2004/0152784 A1 | 8/2004 | March |
| 2004/0229948 A1 | 11/2004 | Summar et al. |
| 2005/0059150 A1 | 3/2005 | Guarino et al. |
| 2005/0182064 A1 | 8/2005 | Burzynski |

(Continued)

FOREIGN PATENT DOCUMENTS

| AU | 2014250643 A1 | 11/2014 |
|---|---|---|
| AU | 2015221466 A1 | 9/2015 |

(Continued)

OTHER PUBLICATIONS

Abraldes et al., "Hemodynamic Response to Pharmacological Treatment of Portal Hypertension and Long-Term Prognosis of Cirrhosis", Hepatol. 2003, 37:902-908.

Aggarwal et al., "Predictors of Mortality and Resource Utilization in Cirrhotic Patients Admitted to the Medical ICU", Chest, 2001, vol. 119, Issue 5, pp. 1489-1497.

Albrecht et al., "Contrasting effects of thioacetamide-induced liver damage on the brain uptake indices of ornithine, arginine and lysine: modulation by treatment with ornithine aspartate", Metab Brain Dis., 1996, vol. 11, Issue 3, pp. 229-237.

(Continued)

*Primary Examiner* — Brian J Davis
(74) *Attorney, Agent, or Firm* — Knobbe, Martens, Olson & Bear, LLP

(57) ABSTRACT

Disclosed herein are methods of preventing, treating, and delaying the onset or progression of diseases associated with hepatic stellate cells (HSCs), such as non-alcoholic fatty liver disease (NAFLD), fibrosis, and liver cancer, using ammonia-lowering therapies.

16 Claims, 19 Drawing Sheets

(56) References Cited

U.S. PATENT DOCUMENTS

| | | |
|---|---|---|
| 2006/0045912 A1 | 3/2006 | Truog |
| 2008/0119554 A1 | 5/2008 | Jalan et al. |
| 2010/0280119 A1 | 11/2010 | Anderson et al. |
| 2012/0157526 A1 | 6/2012 | Jalan et al. |
| 2012/0208885 A1 | 8/2012 | Anderson et al. |
| 2012/0259016 A1 | 10/2012 | Jalan et al. |
| 2013/0211135 A1 | 8/2013 | Anderson et al. |
| 2013/0296429 A1 | 11/2013 | Anderson et al. |
| 2014/0142186 A1 | 5/2014 | Scharschmidt et al. |
| 2014/0288327 A1 | 9/2014 | Anderson et al. |
| 2015/0133684 A1 | 5/2015 | Anderson et al. |
| 2015/0251990 A1 | 9/2015 | Anderson et al. |
| 2016/0338982 A1 | 11/2016 | Ruettimann et al. |
| 2017/0135973 A1 | 5/2017 | Wang et al. |
| 2017/0189364 A1 | 7/2017 | Jalan et al. |
| 2018/0161293 A1 | 6/2018 | Jalan et al. |
| 2018/0221320 A1 | 8/2018 | Rose et al. |

FOREIGN PATENT DOCUMENTS

| | | |
|---|---|---|
| CA | 2763894 A1 | 1/2011 |
| CN | 1383815 | 12/2002 |
| CN | 101010087 A | 8/2007 |
| EP | 1179347 | 2/2002 |
| EP | 1334722 | 8/2003 |
| EP | 1374863 | 1/2004 |
| EP | 1541141 | 6/2005 |
| FR | 2113774 A1 | 6/1972 |
| GB | 965637 | 8/1964 |
| GB | 1067742 | 5/1967 |
| GB | 1080599 | 8/1967 |
| GB | 1310658 | 3/1973 |
| GB | 1507951 | 4/1978 |
| JP | H05-221858 | 8/1993 |
| JP | 2008-521784 | 6/2008 |
| JP | 2011-236160 | 11/2011 |
| JP | S54-163518 | 12/2011 |
| MX | PA03009902 A | 5/2005 |
| WO | WO 1985/04805 | 11/1985 |
| WO | WO 1987/05297 | 9/1987 |
| WO | WO 1997/30167 | 8/1997 |
| WO | WO 2000/071151 | 11/2000 |
| WO | WO 2002/034255 | 5/2002 |
| WO | WO 2002/074302 | 9/2002 |
| WO | WO 2003/037378 | 5/2003 |
| WO | WO 2003/045372 | 6/2003 |
| WO | WO 2003/086074 | 10/2003 |
| WO | WO 2004/019928 | 3/2004 |
| WO | WO 2005/053607 | 6/2005 |
| WO | WO 2005/082023 | 9/2005 |
| WO | WO 2006/056794 | 6/2006 |
| WO | WO 2006/059237 | 6/2006 |
| WO | WO 2010/115055 | 10/2010 |
| WO | WO 2010/144498 | 12/2010 |
| WO | WO 2012/048043 | 4/2012 |
| WO | WO 2014/081977 | 5/2014 |
| WO | WO 2016/172112 | 10/2016 |

OTHER PUBLICATIONS

Albrecht et al., "Increase of the brain uptake index for L-ornithine in rats with hepatic encephalopathy", Neuroreport., 1994, vol. 5, Issue 6, pp. 671-673.
Al-Hassnan et al., "The relationship of plasma glutamine to ammonium and of glycine to acid-base balance in propionic acidaemia", J. Inherit. Metab. Dis., 2003, vol. 26, pp. 89-91.
Al Sibae et al., "Current Trends in the Treatment of Hepatic Encephalopathy", Ther Clin Risk Manag. Jun. 2009, 5(3): 617-626.
Als-Nielsen et al.,, Non-Absorbable Disaccharides for Hepatic Encephalopathy: Systematic Review of Randomised Trials, BMJ, 2004, p. 1-6.
Anadiotis et al., "Ornithine transcarbamylase deficiency and pancreatitis", J Pediatr, 2001, vol. 138, pp. 123-124.
Anonymous "Sodium phenylbutyrate for urea cycle enzyme deficiencies." [No authors listed], Med Lett Drugs Ther., Nov. 22, 1996, vol. 38, Issue 988, pp. 105-106.
Bachmann et al., "Ammonia toxicity to the brain and creatine", Molecular Genetics and Metabolism, 2004, vol. 81, pp. S52-S57.
Balata et al., "Induced hyperammonemia alters neuropsychology, brain MR spectroscopy and magnetization transfer in cirrhosis,", Hepatology, 2003, vol. 4, Issue 37, pp. 931-939.
Batshaw et al., "Alternative pathway therapy for urea cycle disorders: twenty years later", J Pediatr. 2001, 138(1 Suppl): S46-S55.
Batshaw et al., "Effect of sodium benzoate and sodium phenylacetate on brain serotonin turnover in the Ornithine transcarbamylase-deficient sparse-fur mouse", Pediatric Research, 1988, vol. 23, Issue 4, pp. 368-374.
Beale et al., "Early enteral supplementation with key pharmaconutrients improves sequential organ failure assessment score in critically ill patients with sepsis: outcome of a randomized, controlled, double blind trial,", Crit Care Med., 2008, vol. 1, Issue 36, pp. 131-144.
Berg et al., "Pharmacokinetics and cerebrospinal fluid penetration of phenylacetate and phenylbutyrate in the non-human primate", Cancer Chemother Pharmacol. May 2001, 47(5): 385-390. Abstract Only.
Berge et al., "Pharmaceutical Salts", J Pharm Sci, 1977, vol. 66, pp. 1-19.
Berry et al., "Long-term management of patients with urea cycle disorders", J Pediatri, 2001, vol. 138, Issue 1, pp. S56-S61.
Bighley et al., "Salt Forms of Drugs and Absorption" in Encyclopedia of Pharmaceutical Technology, Marcel Dekker, Inc. New York, 1996, pp. 453-499.
Blei et al., Pathophysiology of Cerebral Edema in Fulminant Hepatic Failure, Journal of Hepatology, 1999, pg. 771-776, vol. 31, Denmark.
Bleichner, et al., "Frequency of infections in cirrhotic patients presenting with acute gastrointestinal haemorrhage", British Journal of Surgery, 1986, vol. 73, Issue 9, pp. 724-726.
Bongers et al., "Exogenous glutamine: the clinical evidence,", Crit Care Med., 2007, vol. 9 Suppl, Issue 35, pp. S545-S552.
Bosoi et al., "Minimal Hepatic Encephalopathy Renders the Brain Susceptible to Hypotension-Induced Neuronal Cell Loss in BDL Rats", A19 from The 12th Annual Canadian Association for Study of the Liver Meeting, Feb. 2016; CA J Gastroenter Hepatol. (Feb 2016) p. 14.
Braga et al., "Crystal Polymorphism and Multiple Crystal Forms", Struct Bond, 2009, 132: 25-50 [pub online Feb. 25, 2009].
Briggs et al., "Effect of Ornithine and Lactate on Urea Synthesis in Isolated Hepatocytes", Biochem J, 1976, vol. 160, pp. 205-209.
Bruha et al., "Effect of carvedilol on portal hypertension depends on the degree of endothelial activation and inflammatory changes", Scand J Gastroenter. 2006, 41: 1454-1463.
Brunquell et al., "Electroencephalographic findings in ornithine transcarbamylase deficiency", J Child Neurol, 1999, vol. 14, Issue 8, pp. 533-536.
Brusilow et al., "Amino acid acylation: A mechanism of nitrogen excretion in inborn errors of urea synthesis", Science, 1980, vol. 207, pp. 659-661.
Brusilow et al., "Treatment of episodic hyperammonemia in children with inborn errors of urea synthesis", The New England Journal of Medicine, 1984, vol. 310, Issue 25, pp. 1630-1634.
Burlina et al., "Long-term treatment with sodium phenylbutyrate in ornithine transcarbamylase-deficient patients", Molecular Genetics and Metabolism, 2001, vol. 72, pp. 351-355.
Butterworth, "Pathophysiology of hepatic encephalopathy: a new look at ammonia", Metab Brain Dis., 2002, vol. 17, Issue 4, pp. 221-227.
Butterworth, "Neuronal cell death in hepatic encephalopathy", Metab Brain Dis. Dec. 2007, 22(3-4): 309-320.
Byrn et al., "Pharmaceutical Solids: A Strategic Approach to Regulatory Considerations", Pharma Res. 1995, 12(7): 945-954.
Caira, M.R., "Crystalline Polymorphism of Organic Compounds", Topic in Current Chemistry 1998, 198: 163-208.
Callado França, et al., Five Days of Ceftriaxone to Treat Spontaneous Bacterial Peritonitis in Cirrhotic Patients, Journal of Gastroenterology, Feb. 2002, p. 119-122 vol. 37, No. 2, Springer, Japan.

(56) References Cited

OTHER PUBLICATIONS

Cavarec et al., "Molecular cloning and characterization of a transcription factor for the copia retrotransposon with homology to the BTB-Containing Lola Neurogenic Factor", Mol. Cell. Biol., 1997, vol. 17, Issue 1, pp. 482-494.
Chainuvati et al., "Ornicetil on encephalopathy. Effect of ornicetil (ornithine alpha-ketoglutarate) on encephalopathy in patients with acute and chronic liver disease", Acta Hepatogastro., 1977, vol. 24, Issue 6, pp. 434-439.
Chawla et al., "Challenges in Polymorphism of Pharmaeuticals", CRIPS Mar. 2004, 5(1): 9-12.
Chen et al., "Continuous arteriovenous hemodiafiltration in the acute treatment of hyperammonaemia due to ornithine transcarbamylase deficiency", Renal Failure, 2000, vol. 22, Issue 6, pp. 823-836.
Ciećko-Michalska et al., "Pathogenesis of Hepatic Encephalopathy", Gastroenter Res Practice 2012, 2012: 7 pages.
Clément et al., "Bile-ligated rats are susceptible to hypotension-induced neuronal cell loss: Implications for persisting neurological complications following liver transplantation", Posters P0012; J Hepatol. Apr. 2015, 62(Suppl. 2): S295.
Clemmesen, et al., Cerebral Herniation in Patients With Acute Liver Failure is Correlated with Arterial Ammonia Concentration, Hepatology, Mar. 1999, p. 648-653, Vo. 29, No. 3, American Association for the Study of Liver Diseases.
ClinicalTrails.gov; William Lee, Med. Uni. S.C.; "Safety Study of Ornithine Phenylacetate to Treat Patients with Acute Liver Failure (STOP-ALF)", ID #NCT01548690; Feb. 2012; 7 pages.
Clinical Trial NCT01847651; "Brain Muscle Axis During Treatment of Hepatic Encephalopathy With L-ornithine L-aspartate", first received May 2, 2013, https://clinicaltrials.gov/ct2/show/NCT01847651 retrieved Jun. 7, 2017; 4 pages.
Darmaun et al., "Phenylbutyrate-induced glutamine depletion in humans; effect on leucine metabolism", Am J Physiol Endocrinol Metab., 1998, vol. 274, pp. E801-E807.
Database WPI, Section CH, Week 200331, Derwent Publications Ltd., London, GB; XP002364873 & CN 1383815 A (LIU W), Dec. 11, 2002 (Abstract Only).
Davies, et al., "L-ornithine and phenylacetate synergistically produce sustained reduction in ammonia and brain water in cirrhotic rats", Hepatology Jul. 2009, 50(1): 155-164.
Dejong et al., "Altered glutamine metabolism in rat portal drained viscera and hindquarter during hyperammonemia", Gastroenterology, 1992, vol. 103, Issue 3, pp. 936-948.
Del Rosario et al., Hyperammonemic encephalopathy, J Clin Gastroenterol, 1997, vol. 25, Issue 4, pp. 682-684.
Desjardins et al., "Effect of portacaval anastomosis on glutamine synthetase protein and gene expression in brain, liver and skeletal muscle", Metab Brain Dis., 1999, vol. 14, Issue 4, pp. 273-280.
Dewhirst et al., "Phylogeny of the defined murine microbiota: Altered Schaedler Flora", Appl. Environ Microbiol. 1999, 65(8): 3287-3292.
Dunitz et al., "Disappearing Polymorphs", Acc Chem Res. 1995, 28: 193-200.
Enns et al., "Survival after treatment with phenylacetate and benzoate for urea-cycle disorders,", N Engl J Med., 2007, vol. 22, Issue 356, pp. 2282-2292.
Fabbri et al., Unresponsiveness of Hepatic Nitrogen Metabolism to Glucagon Infusion in Patients with Cirrhosis: Dependence on Liver Cell Failure, Hepatology 1993, 18(1): 28-35.
Garcia-Tsao, MD, et al., Management and Treatment of Patients with Cirrhosis and Portal Hypertension: Recommendations from the Department of Veterans Affairs Hepatitis C Resource Center Program and the National Hepatitis C Program, Am J Gastroenterol, 2009, p. 1802-1829, Vo. 104.
Garden et al., "Prediction of outcome following acute variceal haemorrhage", Br J Surg., 1985, vol. 72, pp. 91-95.
Gebhardt et al., "Treatment of cirrhotic rats with L-Ornithine-L-Aspartate enhances urea synthesis and lowers serum ammonia levels", J Pharm Exp Thera., 1997, vol. 283, Issue 1, pp. 1-6.

Gonzalez-Navajas et al., "Bacterial DNA in patients with cirrhosis and sterile ascites. Its role as a marker of bacterial translocation and prognostic tool,", Rev Esp Enferm Dig., 2007, vol. 10, Issue 99, pp. 599-603.
Gordon, "Ornithine transcarbamylase deficiency: a urea cycle defect", European Journal of Paediatric Neurology, 2003, vol. 7, pp. 115-121.
Grace et al., "Prevention of initial variceal hemorrhage", Gastroenter Clin North Am., 1992, vol. 21, Issue 1, pp. 149-161.
Grant, D.J.W., "Theory and Origin of Polymorphism" Chapter 1 from Polymorphism in Pharmaceutical Solids, Brittain, Harry G. [Ed.]; Marcel Dekker, Inc., 1999; pp. 1-11.
Greenstein et al., Studies on the Metabolism of Amino Acids and Related Compounds in Vivo. III. Prevention of Ammonia Toxicity by Arginine and Related Compounds, Arch Biochem Biophys, 1956, vol. 64, Issue (2):, pp. 342-354.
Grossi et al., "Amino acids mixtures in prevention of acute ammonia intoxication in dogs", Arch Surg, 1967, vol. 94, pp. 261-266.
Guillory, J.K., "Generation of Polymorphs, Hydrates, Solvates, and Amorphous" Chapter 5 from Polymorphism in Pharmaceutical Solids, Brittain, Harry G. [Ed.]; Marcel Dekker, Inc., 1999, pp. 183-226.
Häberle et al., Hyperammonämie: Ursachen, Diagnostik, Therapie, Dtsch Med Wochenschr, 2004, vol. 129; pp. 1430-1433.
Hamberg, Ole et al., Effects of an Increase in Protein Intake on Hepatic Efficacy for Urea Synthesis in Healthy Subjects and in Patients with Cirrhosis, Journal of Hepatology, 1992, pp. 237-243, Elsevier Science Publishers B.V.
Hass et al., "Detection of subclinical and overt hepatic encephalopathy and treatment control after L-Ornithine-L-Aspartate medication by magnetic resonance spectroscopy (1H-MRS)", Z Gastroenterol, 2005, vol. 43, pp. 373-378.
Häussinger et al., "Hepatic encephalopathy in chronic liver disease: a clinical manifestation of astrocyte swelling and low-grade cerebral edema?", J Hepatol., 2000, vol. 32, Issue 6, pp. 1035-1038.
Herlong et al., "The use of ornithine salts of branched-chain ketoacids in portal-systemic encephalopathy", Ann Intern Med., 1980, vol. 93, Issue 4, pp. 545-550.
Hirayama et al., [Eds], "Organic compound crystal produced handbook—Principles and know-how", Maruzen Co., Ltd., Japan; (Jul. 2008), pp. 17-23, 37-40, 45-51 and 57-65; 31 pages.
Honda M et al., "Successful treatment of severe hyperammonemia using sodium phenylacetate powder prepared in hospital pharmacy", Biol. Pharm. Bull., Sep. 2002, 25(9): 1244-1246.
Hopkins Medicine (http://www.hopkinsmedicine.org/gastroenterology_hepatology/_pdfs/liver/portal_hypertension.pdf; accessed Jun. 22, 2016); 13 pages.
Hursthouse et al., "Why Do Organic Compounds Crystallise Well or Badly or Ever so Slowly? Why is Crystallisation Nevertheless Such a Good Purification Technique?", Organic Process Research & Development, 2009, 13:1231-1240.
Igarashi et al., "Determination of ornithine conjugates of some carboxylic acids in birds by high-performance liquid chromatography", Chem Pharm Bull, 1992, vol. 40, Issue 8, pp. 2196-2198.
Inoue et al., "Biochemical analysis of decreased ornithine transport activity in the liver mitochondria from patients with hyperornithinemia, hyperammonemia and homocitrullinuria", Biochim Biophys Acta., 1988, vol. 964, Issue 1, pp. 90-95.
International Search Report and Written Opinion dated Mar. 11, 2016 in Application No. PCT/US2015/062223, filed Nov. 23, 2015.
Iyer et al., "Mouse model for human arginase deficiency", Mol Cell Biol., 2002, vol. 22, Issue 13, pp. 4491-4498.
Jalan et al., "Acute-on-chronic liver failure: pathophysiological basis of therapeutic options", Blood Purif, 2002, vol. 20, pp. 252-261.
Jalan et al., "Moderate hypothermia in patients with acute liver failure and uncontrolled intracranial hypertension,", Gastroenterology, 2004, vol. 5, Issue 127, pp. 1338-1346.
Jalan et al., "The molecular pathogenesis of hepatic encephalopathy", The International Journal of Biochemistry & Cell Biology, 2003, vol. 35, pp. 1175-1181.

(56) References Cited

OTHER PUBLICATIONS

Jalan et al., L-Ornithine Phenylacetate (OP): A Novel Treatment for Hyperammonemia and Hepatic Encephalopathy, Medical Hypotheses, 2007, 69(5): 1064-1069, Elsevier Ltd.

Jalan et al., Treatment of Hyperammonemia in Liver Failure: A Tale of Two Enzymes, Gastroenterology, 2009, p. 2048-2051, vol. 1236.

Jalan Intracranial Hypertension in Acute Liver Failure: Pathophysiological Basis of Rational Management, Seminars in Liver Disease, 2003, p. 271-282, vol. 23, No. 3, Thieme Medical Publisheres, Inc., New York, Ny, Usa.

James et al., "The conjugation of phenylacetic acid in man, sub-human primates and some non-primate species", Proc R Soc Lond B., 1972, vol. 182, pp. 25-35.

Jeyamani et al., Hepatitis E virus and acute-on-chronic liver failure,, Indian J Gastroentero., 2004, vol. 23, Issue 2, pp. 45-46.

Jiang et al., "L-Ornithine-1-aspartate in the management of hepatic encephalopathy: a meta-analysis", J Gastroenterol Hepatol. 2009, 24(1): 9-14; available online: Sep. 28, 2008.

Jover-Cobos et al., Ornithine phenylacetate revisited; Metabolic Brain Disease 2013, 28(2): 327-331.

Kaiser, S. et al., Ammonia and Glutamine Metabolism in Human Liver Slices: New Aspects on the Pathogenesis of Hyperammonaemia in Chronic Liver Disease, European journal of Clinical Investigation , 1988, vol. 18, pp. 535-542.

Kasumov et al., "New secondary metabolites of phenylbutyrate in humans and rats", Drug Metab Dispos., 2004, vol. 32, Issue 1, pp. 10-19.

Katayama, "Ammonia metabolism and hepatic encephalopathy", Hep. Research, 2004, vol. 30, Issue 1, pp. S71-S78.

Khan et al.,, Frequency of Spontaneous Bacterial Peritonitis in Cirrhotic Patients with Ascites Due to Hepatitis C Virus and Efficacy of Ciprofloxacin in its Treatment, Gomal Journal of Medical Sciences, Jul.-Dec. 2009, p. 149-154, vol. 7, No. 2.

Kircheis et al., "Therapeutic efficacy of L-ornithine-L-aspartate infusions in patients with cirrhosis and hepatic encephalopathy: results of a placebo-controlled, double blind study,", Hepatology, 1997, vol. 6, Issue 25, pp. 1351-1360.

Kojima et al., "Effective Solid Form Selection for the Pharmaceutical Development", J Pharma Science Tech. Sep. 2008, 68(5): 344-349.

Larsen et al., "Alternative Pathway Therapy for Hyperammonemia in Liver Failure"; Hepatolory, Jul. 2009, 50(1): 3-5.

Lee et al., Acute Liver Failure: Summary of a Workshop, Hepatology, Apr. 2008, p. 1401-1415, vol. 47, No. 4,.

Lee, W. M., Acetaminophen-Related Acute Liver Failure in the United States, Hepatology Research, 2008, p. S3-S8, vol. 38, Suppl. 1, The Japan Society of Hepatology.

Lee et al., "Phase 2 Comparison of a Novel Ammonia Scavenging Agent with Sodium Phenylbutyrate in Patients with Urea Cycle Disorders: Safety, Pharmacokinetics and Ammonia Control", Mol Genet Metab. Mar. 2010, 100(3): 221-228.

Linderoth et al., "Short-term prognosis of community-acquired bacteremia in patients with liver cirrhosis or alcoholism: A population-based cohort study,", Alcohol Clin Exp Res., 2006, Issue 30, pp. 636-641.

Lopez-Talavera et al., "Thalidomide Inhibits Tumor Necrosis Factor alpha, Decreases Nitric Oxide Synthesis, and Ameliorates the Hyperdynamic Circulatory Syndrome in Portal-Hypertensive Rats", Hepatology, 1996, 23(6): 1616-1621.

Lucero et al., "The Role of Sarcopenia and Frailty in Hepatic Encephalopathy Management", Clin Liver Dis. Aug. 2015, 19(3): 507-528.

Lukkarinen, M. et al., Effect of Lysine Infusion on Urea Cycle in Lysinuric Protein Intolerance, Metabolism, May 2000, 49(5): 621-625.

Lukkarinen, M. et al., Oral Supplementation Corrects Plasma Lysine Concentrations in Lysinuric Protein Intolerance, Metabolism, Jul. 2003, 52(7): 935-938.

MacArthur et al., "Pharmacokinetics of sodium phenylacetate and sodium benzoate following intravenous administration as both a bolus and continuous infusion to healthy adult volunteers", Molecular Genetics and Metabolism, 2004, vol. 81, pp. S67-S73.

Maestri et al., "Long-term treatment of girls with ornithine transcarbamylase deficiency", N Engl J Med., 1996, vol. 335, Issue 12, pp. 855-859.

Maestri et al., "Prospective treatment of urea cycle disorders", J Pediatr., 1991, vol. 119, Issue 6, pp. 923-928.

Maev I.V. Application of L-ornitine-L-aspartate in complex therapy of hepatic encephalopathy in liver cirrhosis patients (Engl. Title) koloproktologii, 2002, No. 6, pp. 60-66.

Maier et al., Originalien Activities of Urea-Cycle Enzymes in Chronic Liver Disease, Klinische-Wochenschrift, 1979, vol. 67, pp. 661-665, Springer-Verlag.

Maier, "Therapie der hepatischen Enzephalopathie", Dtsch med Wschr., 1988, vol. 113, pp. 1886-1889.

Matsuoka et al., "Advanced Crystallization Technology of Organic Materials—Control of Size, Morphology, Polymorph and Purity", Pharm Tech, Japan (May 2003) 19(6): 91(955)-101(965).

Mederacke et al., "High-yield and high-purity isolation of hepatic stellate cells from normal and fibrotic mouse livers", Nat Protoc. Feb. 2015, 10(2): 305-315.

Meijer et al., Nitrogen Metabolism and Ornithine Cycle Function, Physiological Reviews, Jul. 1990, vol. 70, No. 3, pp. 701-748, The American Physiological Society.

Mendenhall et al., "A new therapy for portal systemic encephalopathy", The American Journal of Gastroenterology, 1986, vol. 81, Issue 7, pp. 540-543.

Mihm et al., "Effect of L-ornithine-L-aspartate (LOLA) on neurometabolites in hepatic encephalopathy (HE)", Hepatology, 2001, vol. 34, Issue 4, pp. 543A.

Mizock et al., "Septic Encephalopathy—Evidence for altered phenylalanine metabolism and comparison with hepatic encephalopathy", Arch Intern Med, 1990, vol. 150, pp. 443-449.

Mizock, Nutritional Support in Hepatic Encephalopathy, Nutrition, 1999, pp. 220-228, vol. 15, No. 3, Elsevier Science Inc.

Mizutani et al., "Hyperargininemia: Clinical course and treatment with sodium benzoate and phenylacetic acid", Brain Dev., 1983, vol. 5, Issue 6, pp. 555-563.

Mohamed et al., "Effect of toll-like receptor 7 and 9 targeted therapy to prevent the development of hepatocellular carcinoma", Liver Int. Mar. 2015, 35(3): 1063-1076.

Mohammad R.A. et al., Combination therapy for the treatment and prevention of hepatic encephalopathy; Ann Pharmacother. (Nov. 2012) 46(11): 1559-1563.

Moinard et al.,, "Effects of Ornithine 2-Oxoglutarate on Neutrophils in Stressed Rates: Evidence for the Involvement of Nitric Oxide and Polyamines", Clin Sci, 2002, vol. 102, Issue 3, pp. 287-295, London, England.

Mokhtarani, M. et al., "Urinary Phenylacetylglutamine as Dosing Biomarker for Patients with Urea Cycle Disorders", Mol Genet Metab. (Nov. 2012) 107(3): 308-314.

Mookerjee et al., "Neutrophil dysfunction in alcoholic hepatitis superimposed on cirrhosis is reversible and predicts the outcome,", Hepatology, 2007, vol. 3, Issue 46, pp. 831-840.

Mookerjee et al., "Increased gene and protein expression of the novel eNOS regulatory protein NOSTRIN and a variant in alcoholic hepatitis", Gastroenterology Jun. 2007, 132(7): 2533-2541.

Mouille et al., "Adaptative increase of ornithine production and decrease of ammonia metabolism in rat colonocytes after hyperproteic diet ingestion", Am J Gastrointest Liver Physiol., 2004, 287(2), G344-G351.

Nance et al., "Ammonia production in germ-free Eck fistula dogs", Surgery, 1971, vol. 70, Issue 2, pp. 169-174.

Navasa et al., "Bacterial infections in liver cirrhosis,", Ital J Gastroenterol Hepatol., 1999, vol. 7, Issue 31, pp. 616-625.

Nema et al., "Excipients and Their Role in Approved Injectable Products: Current Usage and Future Directions", PDA J Pharm Sci Technol. 2011, 65(3): 287-332.

Newsholme et al., "Glutamine metabolism by lymphocytes, macrophages, and neutrophils: its importance in health and disease,", J Nutr Biochem., 1999, vol. 6, Issue 10, pp. 316-324.

(56) References Cited

OTHER PUBLICATIONS

Newsholme, "Why is L-glutamine metabolism important to cells of the immune system in health, postinjury, surgery or infection?", J Nutr., 2001, vol. 9 Suppl, Issue 131, pp. 2515S-2522S.

Ocera Therapeutics, Inc., News Release: Ocera Completes Interim Analysis of OCR-002 in Phase 2b STOP-HE Study for the Treatment of Acute Hepatic Encephalopathy; Globe Newswire; Apr. 1, 2015, 2 pages.

Ocera Therapeutics, Inc., News Release: Ocera Announces Positive Phase 1 Results for Oral OCR-002 in Development for the Prevention of Acute Hepatic Encephalopathy; Globe Newswire; Nov. 16, 2015, 2 pages.

Ocera Therapeutics, Inc., News Release: Ocera Completes Plasma Data from Pilot Phase 1 Study for Orally-available OCR-002 in Development for the Prevention of Acute Hepatic Encephalopathy; Globe Newswire; Jan. 8, 2016, 3 pages.

Olde Damink et al., "Decreased plasma and tissue isoleucine levels after simulated gastrointestinal bleeding by blood gavages in chronic portacaval shunted rats", Gut, 1997, vol. 40, pp. 418-424.

Olde Damink et al., "Interorgan ammonia and amino acid metabolism in metabolically stable patients with cirrhosis and a TIPSS", Hepatology, 2002, vol. 36, Issue 5, pp. 1163-1171.

Olde Damink et al., "Interorgan ammonia metabolism in liver failure", Neurochemistry International, 2002, vol. 41, pp. 177-188.

Olde Damink et al., "The kidney plays a major role in the hyperammonemia seen after simulated or actual GI bleeding in patients with cirrhosis", Hepatology, 2003, vol. 37, pp. 1277-1285.

Olde Damink et al., Stimulated Liver and Muscle Protein Synthesis by Intravenous Isoleucine Supplementation During a Simulated Variceal Bleed in Patients with Cirrhosis of the Liver, Hepatology, Oct. 2001, AASLD Abstracts #50.

Oria et al., "Ornithine phenylacetate prevents disturbances of motor-evoked potentials induced by intestinal blood in rats with portacaval anastomosis", J Hepatol. Jan. 2012, 56(1): 109-114.

Pauwels et al., "Systemic antibiotic prophylaxis after gastrointestinal hemorrhage in cirrhotic patients with a high risk of infection", Hepatology, 1996, vol. 24, Issue 4, pp. 802-806.

Petrowski et al., "Pharmacologic amino acid acylation in the acute hyperammonemia of propionic acidemia", Journal of Neurogenetics, 1987, vol. 4, pp. 87-96.

Plecko et al., "Partial N-acetylglutamate synthetase deficiency in a 13-year-old girl: diagnosis and response to treatment with N-carbamylglutamate", Eur J Pediatr., 1998, vol. 157, pp. 996-998.

Powell et al., "Compendium of Excipients for Parenteral Formulations", PDA J Pharm Sci Technol. 1998, 52(5): 238-311.

Praphanphoj et al., "Three cases of intravenous sodium benzoate and sodium phenylacetate toxicity occurring in the treatment of acute hyperammonemia", J Inherit Metab Dis., 2000, vol. 23, pp. 129-136.

Puche et al., "Hepatic stellate cells and liver fibrosis", Comprehensive Physiol. 2013, 3:1473-1491.

Qiu et al., "Hyperammonemia-mediated autophagy in skeletal muscle contributes to sarcopenia of cirrhosis", Am J Physiol Endocrinal Metab. Aug. 2012, 303: E983-993.

Qiu et al., "Hyperammonemia in cirrhosis induces transcriptional regulation of myostatin by an NF-kappaB-mediated mechanism", PNAS Nov. 2013, 110(45): 18162-18167.

Rajkovic et al., "Mechanisms of abnormalities in host defences against bacterial infection in liver disease," Clin Sci. (Lond.), 1985, vol. 3, Issue 68, pp. 247-53, London.

Ramaswamy et al., "Mouse model for human arginase deficiency", Mol Cell Biol., Jul. 2002, vol. 22, Issue 13, pp. 4491-4498.

Rees et al., "Effect of L-Ornithine-L-Aspartate on patients with and without TIPS undergoing glutamine challenge: a double blind, placebo controlled trial", Gut, 2000, vol. 47, pp. 571-574.

Riordan et al., "Treatment of hepatic encephalopathy", Curr Concepts, 1997, vol. 337, Issue 7, pp. 473-479.

Rogers, Q. R. et al., Deficiency of Pyrroline-5-Carboxylate Synthase in the Intestinal Mucosa of the Cat, J Nutrition, 1985, 115(1): 146-150.

Rombouts et al., "Determination and Characterization of Tetraspanin-associated Phosphoinositide-4 Kinases in Primary and Neoplastic Liver Cells", In Lipid Signaling Protocols, 2nd Ed. [Waugh M.G.] 2015; Chapter 17, pp. 203-212.

Romero-Gómez et al., "Intestinal glutaminase activity is increased in liver cirrhosis and correlates with minimal hepatic encephalopathy", J Hepatol. 2004, 41: 49-54.

Romero-Gómez et al., "Hepatic encephalopathy in patients with acute decompensation of cirrhosis and acute-on-chronic liver failure", J Hepatol. Feb. 2015, 62(2): 437-447.

Rose et al., "L-Ornithine-L-Aspartate in experimental portal-systemic encephalopathy: therapeutic efficacy and mechanism of action", Metabolic Brain Disease, 1998, vol. 13, Issue 2, pp. 147-157.

Rose et al., "L-Ornithine-L-Aspartate lowers plasma and cerebrospinal fluid ammonia and prevents brain edema in rats with acute liver failure", Hepatology, 1999, vol. 30, Issue 3, pp. 636-640.

Rudman et al., Maximal Rates of Excretion and Synthesis of Urea in Normal and Cirrhotic Subjects, The Journal of Clinical Investigation, Sep. 1973, vol. 52, pp. 2241-2249.

Rukmini et al., "Region-specific changes in CNS muscarinic acetylcholine receptors in a rat model of hyperammonemia", Biochem Pharmacol., 1998, vol. 56, Issue 2, pp. 237-241.

Sanyal et al., Portosystemic Encephalopathy After Transjugular Intrahepatic Portosystemic Shunt: Results of a Prospective Controlled Study, Hepatology, 1994, p. 46-55, vol. 20, No. 1, Pt. 1, The American Association for the Study of Liver Diseases.

Sanyal, A. J., Prediction of Variceal Hemorrhage in Patients with Cirrhosis, UpToDate, Inc., Website (www.uptodate.com), Jan. 2010, UpToDate.

Sarhan et al., "Effects of inhibition of ornithine aminotransferase on thioacetamide-induced hepatogenic encephalopathy", Neurochem Res., 1993, vol. 18, Issue 4, pp. 539-549.

Scaglia et al., "Effect of alternative pathway therapy on branched chain amino acid metabolism in urea cycle disorder patients", Mol Genet Metabolism, 2004, vol. 81, pp. S79-S85.

Sears et al., "Disruption of the blood-brain barrier in hyperammonaemic coma and the pharmacologic effects of dexamethasone and difluoromethyl ornithine", J Neurosci Res., 1985, vol. 14, Issue 2, pp. 255-261.

Seiler et al., "Ornithine aminotransferase activity, liver ornithine concentration and acute ammonia intoxication", Life Sciences, 1989, vol. 45, Issue 11, pp. 1009-1020.

Seiler, "Ornithine aminotransferase, a potential target for the treatment of hyperammonemias", Curr Drug Targets., Sep. 2000, vol. 1, Issue 2, pp. 119-153.

Sen et al., "The pathophysiological basis of acute-on-chronic liver failure", Liver, 2002, vol. 22, Issue Suppl. 2, pp. 5-13.

Shangraw et al., Effect of Liver Disease and Transplantation on Urea Synthesis in Humans: Relationship to Acid-Base Status, AM J Physiol Gastrointest Liver Physiol, 1999, vol. 276, pp. 1145-1152.

Shawcross et al., "Ammonia impairs neutrophil phagocytic function in liver disease,", Hepatology, 2008, vol. 4, Issue 48, pp. 1202-1212.

Shawcross et al., "Dispelling myths in the treatment of hepatic encephalopathy,", Lancet, 2005, vol. 9457, Issue 365, pp. 431-433.

Shawcross et al., "Hyperammonemia impairs neutrophil function", Hepatology, 2005, vol. 42, pp. 537A.

Shen et al., "Engineering the gut microbiota to treat hyperammonemia", J Clin Invest. Jun. 2015, 125(7): 2841-2850.

Shriner et al., "Recrystallization", Chapter 3.5 Preliminary Examination in The Systematic Identification of Organic Compounds, John Wiley & Sons, Inc. New York, 1998, Chapter 3, pp. 78-81.

Simell et al., "Waste nitrogen excretion via amino acid acylation: benzoate and phenylacetate in lysinuric protein intolerance", Pediatric Research, 1986, vol. 20, Issue 11, pp. 1117-1121.

Singh, et al., Changing Epidemiology and Predictors of Mortality in Patients With Spontaneous Bacterial Peritonitis at a Liver Transplant Unit, Clinical Microbiology and Infection, Jun. 2003, p. 531-537, vol. 9, No. 6., European Society of Clinical Microbiology and Infectious Diseases.

Smith et al., "The treatment of inborn errors of the urea cycle", Nature, 1981, vol. 291, Issue 5814, pp. 378-380.

(56) References Cited

OTHER PUBLICATIONS

Soláini et al., "Variations in the plasma concentration of ornithine, citrulline and arginine in acute experimental liver failure" [Article in Italian], Boll Soc Ital Biol Sper., 1981, vol. 57, Issue 7, pp. 705-710.
Stedman's Medical Dictionary; "Encephalopathy", 27th Edition, 2002; 1 page.
Stewart, P. M., et al., Effects of Arginine-Free Meals on Ureagenesis in Cats, American Journal of Physiological, 1981, pp. E310-E315, vol. 241, No. 4, The American Physiological Society.
Stravitz, MD, et al., Intensive Care of Patients with Acute Liver Failure: Recommendations of the U.S. Acute Liver Failure Study Group, Critical Care Medicine, 2007, p. 2498-2508, vol. 35, No. 11, Lippincott Williams & Wilkins.
Suchy et al., Clinical Manifestations and Complications—Typical Clinical Presentation;, Liver Disease in Children, 2nd Edition, 2001, pp. 74-77.
Sugarbaker et al., "The role of the small intestine in ammonia production after gastric blood administration", Ann Surg., 1987, vol. 206, Issue 1, pp. 5-17.
Sukhotnik et al., "Oral glutamine prevents gut mucosal injury and improves mucosal recovery following lipopolysaccharide endotoxemia in a rat,", J Surg Res., 2007, vol. 2, Issue 143, pp. 379-384.
Svanberg et al., "Effects of amino acids on synthesis and degradation of skeletal muscle proteins in humans", Am J Physiol., 1996, vol. 271, Issue 4 Pt1, pp. E718-E724.
Timely Data Resource (TDR), IPD Printable Search Results, "Incidence and Prevalence Database, ICD-9 Code: 567. Peritonitis," <URL:http://www.tdrdata.com/IPD/ipd_searchresultsdataprinter.aspx?SessionGUID=ac0c91d8-7 . . . , Jul. 27, 2010, 7 pages.
Teran et al., "Primary prophylaxis of variceal bleeding in cirrhosis: A cost-effectiveness analysis", Gastroenter., 1997, vol. 112, Issue 2, pp. 473-482.
Thomsen et al., "Experimental nonalcoholic steatohepatitis compromises ureagenesis, an essential hepatic metabolic function", Am J Physiol Gastrointest Liver Physiol. Jun. 2014, 307(3): G295-G301.
Torres-Vega et al., "Delivery of Glutamine Synthetase Gene by Baculovirus Vectors: A Proof of Concept for the Treatment of Acute Hyperammonemia", Gene Ther., Jan. 2015, 33(1): 58-64.
Trebicka et al., Atorvastatin lowers portal pressure in cirrhotic rats by inhibition of RhoA/Roh-kinase and activation of endothelial nitric oxide synthase, Hepatology, 2007, 46(1): 242-253.
Tuchman, M., et al., Management of Inherited Disorders of Ureagenesis, The Endocrinologist, 2002, vol. 12, No. 2, pg. 99-109.
Tuchman, MD et al., "Episodic hyperammonemia in adult siblings with hyperornithinemia, hyperammonemia, and homocitrullinuria syndrome", Arch Neurol., 1990, vol. 47, pp. 1134-1137.
Van Berlo et al., "Is increased ammonia liberation after bleeding in the digestive tract the consequence of complete absence of isoleucine in hemoglobin? A study in pigs", Hepatology, 1989, vol. 10, Issue 3, pp. 315-323.
Van Den Berg et al., "The effect of glutamine-enriched enteral nutrition on intestinal microflora in very low birth weight infants: a randomized controlled trial,", Clin Nutr., 2007, vol. 4, Issue 26, pp. 430-439.
Ventura-Cots et al., Safety of ornithine phenylacetate in cirrhotic decompensated patients: an open-label, dose-escalating, single-cohort study; J Clin Gastroenter. (2013) 47(10): 881-887.
Vilstrup, H. et al., Elimination of Infused Amino Acids From Plasma of Control Subjects and of Patients With Cirrhosis of the Liver, European Journal of Clinical Investigation, 1982, vol. 12, pp. 197-202, Blackwell Scientific Publications.
Vogels et al., "L-ornithine vs L-ornithine-L-aspartate as a treatment for hyperammonemia-induced encephalopathy in rats", J Hepatology, 1997, vol. 26, Issue 1, pp. 174-182.
Walrand S., "Ornithine alpha-ketoglutarate: Could it be a new therapeutic option for sarcopenia?", J Nutr Health Aging. Aug. 2010, 14(7): 570-577.

Wasmuth et al., "Patients with acute on chronic liver failure display 'sepsis-like' immune paralysis,", J Hepatol., 2005, vol. 2, Issue 42, pp. 195-201.
Wright et al., "Reduction in Ammonia with L-Ornithine, Phenylacetate (OP) but not Anti-TNF Prevents LPS Induced Brain Edema in Bile-duct Ligated Cirrhotic Rats", Abstract 773; J Hepatology 2009, 50: S283.
YTREBØ et al., "Interorgan ammonia, glutamate, and glutamine trafficking in pigs with acute liver failure,", Am J Physiol Gastrointest Liver Physiol., 2006, vol. 3, Issue 291, pp. G373-G381.
YTREBØ et al., "L-Ornithine Phenylacetate Attenuates Increased Arterial and Extracellular Brain Ammonia and Prevents Intracranial Hypertension in Pigs with Acute Liver Failure", Hepatology, Jul. 2009, 50(1): 165-174.
Yudkoff et al., "In Vivo Nitrogen Metabolism in Ornithine Transcarbamylase Deficiency", J Clin. Invest., Nov. 1996, 98(9): 2167-2173.
Zetterman, Rowen K., MD, "Complications of Portal Hypertension: Hepatic Encephalopathy", Medscape (Jun. 2011) available online at www.medscape.com/viewarticle/744392; downloaded Dec. 3, 2014; 6 pages.
Zhu Q. et al., Rifaximin Attenuates Bile Duct Ligation Induced Liver Fibrosis and Portal Hypertension Through Inhibition of the TLR4 Pathway; Gastroenterology (May 2011) 140(5) Suppl 1: S903; Abstract 732.
Zhu Q. et al., Intestinal decontamination inhibits TLR4 dependent fibronectin mediated crosstalk between stellate cells and endothelial cells in liver fibrosis in mice; J Hepatol. (Apr. 2012) 56(4): 893-899.
Zieve et al., "Ammonia toxicity: comparative protective effect of various arginine and ornithine derivatives, aspartate, benzoate, and carbamyl glutamate", Metabo Brain Dis., 1986, vol. 1, Issue 1, pp. 25-35.
Zieve et al., "Conditional deficiencies of ornithine or ornithine or arginine", J Am Coll Nutr., 1986, vol. 5, Issue 2, pp. 167-176.
Chung et al., "Cirrhosis and its Complications", Harrison'S Principles of Internal Medicine (16th Edition) (2005) 289, pp. 1858-1869.
Ocera Therapeutics, Inc., News Release: Ocera Initiates Phase 1 Clinical Trial of Oral Drug Candidate OCR-002 for Prevention of Hepatic Encephalopathy; Globe Newswire; Sept 16, 2015, 4 pages.
Schouten et al. "Idiopathic noncirrhotic portal hypertension", Hepatology, Sep. 2011; 54(3):1071-1081.
U.S. Office Action dated Nov. 20, 2017 for U.S. Appl. No. 15/527,999, filed May 18, 2017.
U.S. Notice of Allowance dated Apr. 5, 2018 for U.S. Appl. No. 15/527,999, filed May 18, 2017.
Eurasian Office Action dated Aug. 22, 2018 for corresponding Eurasia Application No. 201790913, filed May 23, 2017.
European Extended Search Report dated Mar. 22, 2018 for corresponding European Application No. 15864248.8, filed Jun. 1, 2017.
Smirnov et al., "Ammonia Neutralization and Urea Synthesis in Cardiac Muscle", Circ Res., 1974, 35(Suppl 3):58-73.
Efrati et al., "Effect of sodium benzoate on blood ammonia response to oral glutamine challenge in cirrhotic patients: a note of caution", Am J Gastroenterol. (2000) 95(12):3574-3578. (Abstract).
Islam et al., "Sorbitol and lactitol reduce body fat and toxic ammonia levels in rats", Nutrition Res. (2007) 27:440-447.
Yoneda et al., "Treatment for non-alcoholic steatohepatitis", Separate Igakuno Ayumi, Digestive diseases-state of arts Ver. 3, Oct. 10, 2006, pp. 370-372. (English version of publication in 13 pages).
Japanese Office Action dated May 14, 2019 for Application No. 2017-527742 (13 pages).
Bosoi et al., "Oral Ornithine Phenylacetate Attenuates Muscle Mass Loss and Prevents Hepatic Encephalopathy in BDL Rats", Abstract 23; J Clin Exper Hepatol. (Feb. 2017) 7:S18-S19.
Canaby et al. "L-Ornithine L-Aspartate (LOLA) as a Novel Approach for Therapy of Non-alcoholic Fatty Liver Disease", Drugs 2019, vol. 79 (Suppl 1), pp. S39-S44 (first published online Jan. 31, 2019).
Clément et al., "Minimal hepatic encephalopathy leads to hypotension-induces neuronal cell loss in BDL rats", Abstract 51; Hepatology (Oct. 2015) 62(Suppl 1):233A-234A.

(56) References Cited

OTHER PUBLICATIONS

Feuerstein et al., Cytokines, Inflammation, and Brain Injury: Role of Tumor Necrosis Factor-α. Cerebrovasc Brain Metab Rev. 1994, 6(4):341-360.

Hyperion Therapeutics, Inc., RAVICTI™ (glycerol phenylbutyrate) Oral Liquid—Highlights of Prescribing Information; Jan. 2013 in 23 pages.

Kalafateli et al., "Impact of muscle wasting on survival in patients with liver cirrhosis", World J Gastroenterol. 2015, 21(24):7357-7361.

Nardelli et al., "Sarcopenia is Risk Factor for Development of Hepatic Encephalophathy After Transjugular Intrahepatic Portosystemic Shunt Placement", Clin Gastroenterol Hepatol. 2017, 15(6):934-936.

Pahan et al., Lovastatin and Phenylacetate Inhibit the Induction of Nitric Oxide Synthase and Cytokines in Rat primary Astrocytes, Microglia, and Macrophages, J Cin Invest. BMJ Group BG, 1997, 100(11):2671-2679.

Roque et al., "32* Pro-inflammatory effects of sodium 4-phenylbutyrate in CF lung epithelial cells containing F508del-CFTR", J Cystic Fibrosis 2007, 6: S7.

Vilatoba et al., Sodium 4-phenylbutyrate protects against liver ischemia reperfusion injury; Surgery, 2005, 138(2):342-351.

24h          40x 24h          40x

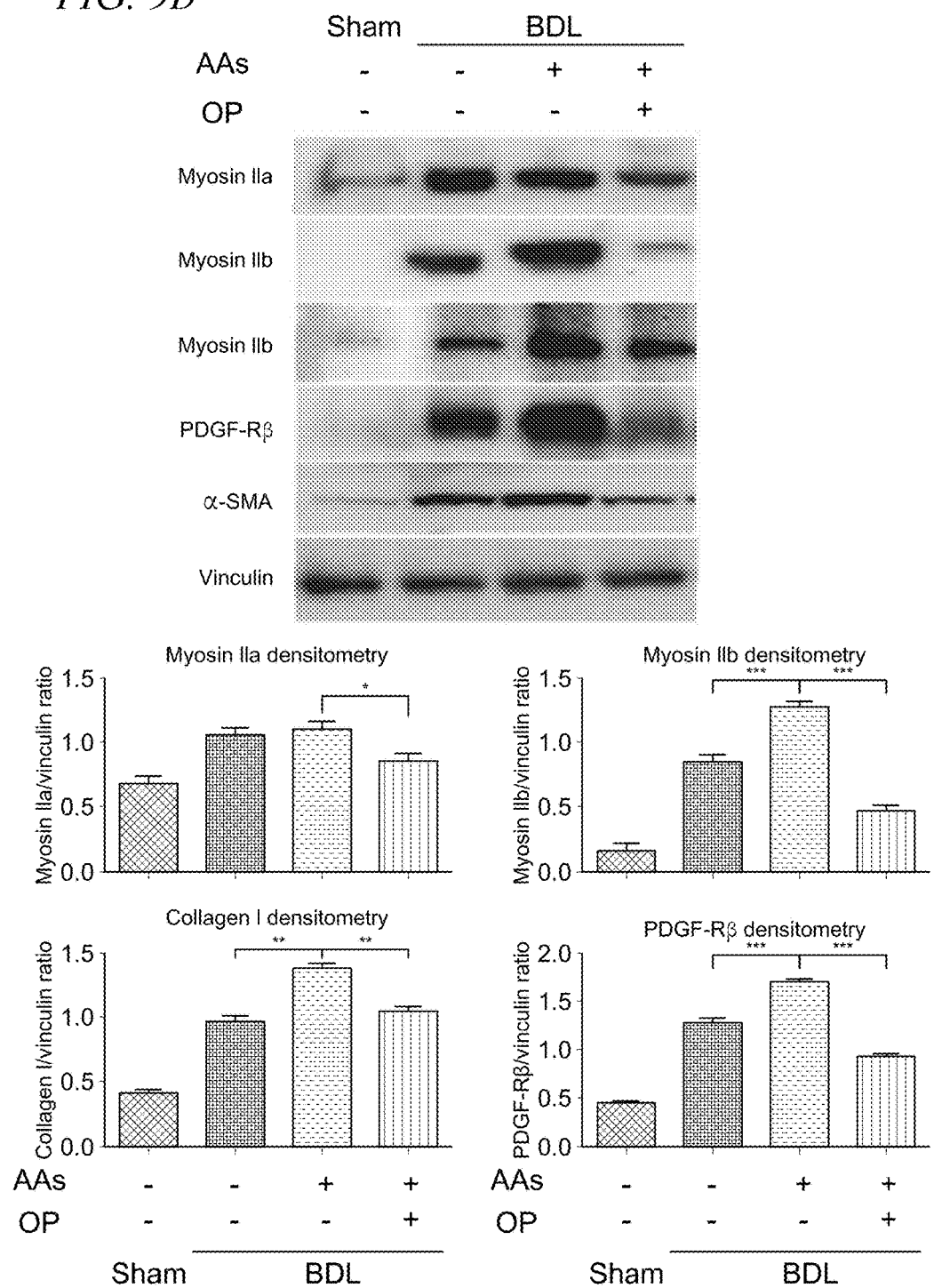

TREATMENT OF DISEASES ASSOCIATED WITH HEPATIC STELLATE CELL ACTIVATION USING AMMONIA-LOWERING THERAPIES

RELATED APPLICATIONS

The present application is a continuation of U.S. patent application Ser. No. 15/527,999, entitled "TREATMENT OF DISEASES ASSOCIATED WITH HEPATIC STELLATE CELL ACTIVATION USING AMMONIA-LOWERING THERAPIES," filed on May 18, 2017, which is a U.S. national phase under 35 U.S.C. § 371 of International Application No. PCT/US2015/062223, filed on Nov. 23, 2015, which claims priority under 35 U.S.C. § 119(e) to U.S. Provisional Application No. 62/083,814, filed on Nov. 24, 2014, which is herein expressly incorporated by reference in its entirety.

BACKGROUND

Field

The present application relates to the fields of pharmaceutical chemistry, biochemistry and medicine. One aspect relates to the treatment and/or prevention of diseases associated with hepatic stellate cell (HSC) activation using ammonia-lowering therapies.

Description of the Related Art

Hepatic stellate cells (HSCs) are pericytes found in the perisinusoidal space of the liver. Within the liver, stellate cells play an important role in maintaining architectural integrity of the liver and are involved in fibrosis and liver cancer development. In normal liver, HSCs are in a quiescent state. When the liver is damaged, HSCs can change into an activated state. The activated stellate cell is characterized by proliferation, contractility and chemotaxis. Various diseases can result from the activation of HSCs, for example, non-alcoholic fatty liver disease (NAFLD), fibrotic conditions, and liver cancer.

Various prevention, treatment and management strategies for diseases associated with the activation of HSCs are currently available depending upon the severity of the symptoms. There is a need for additional therapies for treating or preventing those diseases.

SUMMARY

Some embodiments disclosed herein provides a method of treating a disease associated with hepatic stellate cell (HSC) activation, wherein the method comprises performing an ammonia-lowering therapy on a subject in need thereof. Also disclosed is a method of delaying the onset or progression of a disease associated with HSC activation, wherein the method comprises performing an ammonia-lowering therapy on a subject in need thereof. In some embodiments, performing the ammonia-lowering therapy comprises administering an ammonia-lowering agent to the subject.

In some embodiments, the disease associated with HSC activation is non-alcoholic fatty liver disease (NAFLD). The NAFLD can be, for example, non-alcoholic steatohepatitis (NASH) or steatosis.

In some embodiments, the disease associated with HSC activation is liver cancer. In some embodiments, the disease associated with HSC activation is a fibrotic condition. The fibrotic condition can be, for example, liver fibrosis. In some embodiments, the subject is suffering from non-alcoholic fatty liver disease (NAFLD).

Some embodiments provide a method of preventing non-alcoholic fatty liver disease (NAFLD), wherein the method comprises performing an ammonia-lowering therapy on a subject in need thereof. For example, the NAFLD can be non-alcoholic steatohepatitis (NASH) or steatosis. In some embodiments, performing the ammonia-lowering therapy comprises administering an ammonia-lowering agent to the subject.

In some embodiments, the ammonia-lowering agent is, or comprises, a magnesium phosphate product (MGP), glycerol phenylbutyrate (GPB), sodium phenylacetate, sodium phenylbutyrate (NaPBA), glutamine, sodium benzoate, L-arabinose, a laxative, an antibiotic, ornithine in combination with at least one of phenylacetate and phenylbutyrate, or any combination thereof. In some embodiments, the ammonia-lowering agent is, or comprises, ornithine in combination with at least one of phenylacetate and phenylbutyrate.

In the methods disclose herein, in some embodiments, separate pharmaceutically acceptable salts of the ornithine and at least one of phenylacetate and phenylbutyrate are administered to the subject. In some embodiments, at least one of phenylacetate and phenylbutyrate is administered as a sodium phenylacetate or sodium phenylbutyrate. In some embodiments, the ornithine is administered as a free monomeric amino acid or physiologically acceptable salt thereof. In some embodiments, the ornithine and phenylacetate is administered as ornithine phenylacetate.

In some embodiments, the administration is oral, intravenous, intraperitoneal, intragastric, or intravascular administration. In some embodiments, the administration is intravenous administration. In some embodiments, the administration is oral administration

BRIEF DESCRIPTION OF THE DRAWINGS

FIG. 1A shows ammonia inhibits DNA synthesis (BrdU) and metabolic activity (MTS), and FIG. 1B shows the inhibition is achieved without inducing cell death. FIG. 1C shows that ammonia induced strong morphological changes in a dose-dependent manner i.e. from myofibroblast-like cells into spindle like fibroblasts as was observed by light microscopy and by Neutral Red cell viability test (20×, 40×). Bar graphs show means of three independent values±SD. *$P<0.05$, $P<0.01$ and *$P<0.001$ vs. corresponding values of serum free medium (SFM).

FIG. 2A are Transmission Electron Microscopy (TEM) images showing that ammonia in a dose-dependent manner caused dramatic morphological changes with appearance of cytoplasmic vacuoles (V=vacuoles; N=nucleus). FIG. 2B shows recovery of cell proliferation after depletion of ammonia-rich culture medium. Bar graphs show means of three independent values±SD. *$P<0.05$ and ***$P<0.001$ vs. SFM. FIGS. 2C and 2D depicts results from a collagen gel contraction assay showing that ammonia induces hHSC contraction. Bar graphs show means of 2 independent experiments (values±SD. *$P<0.05$ and

**P<0.01 vs. corresponding values of SFM. FIG. 2E shows that ammonia-induced HSC contraction coincides with changes in morphology. FIG. 2F shows that prolonged treatment (72 h) with ammonia induces in a dose-dependent manner the re-organization of filamentous actin (TRITC-Phalloidin staining).

FIG. 3A shows that prolonged treatment of hHSC with ammonia for 72 hours induces ROS production in hHSC. The formation of reactive oxygen species (ROS) was measured using Image-IT™ LIVE Green Reactive Oxygen Species Detection Kit. In FIG. 3B, mean fluorescence intensity (MFI) of ROS signal was normalized according to the number of cells (Hoechst 33342), and expressed as percentage of control. Bar graphs show means of three independent values±SD. *P<0.001 vs corresponding values of SFM. FIG. 3C shows that jyperammonemia increases mRNA expression level of ROS marker SOD2 at 3 and 24 hours. Bar graphs show means of 2 independent values±SD. *P<0.001 vs corresponding values of SFM.

FIG. 4A shows that ammonia affects protein expression of α-SMA, vimentin, PDGF-Rβ, Myosin IIa and IIb, and p-38 MAPK. FIG. 4B shows that ammonia induces up-regulation of MMP2 mRNA whereas TIMP1 mRNA is down-regulated. FIG. 4C shows that Interleukin 1β and Interleukin IL6 mRNA expression are upregulated. Bar graphs show means of three independent values±SD. *P<0.05, P<0.01 and *P<0.001 vs. corresponding values of SFM.

FIGS. 5A-B show hyperammonemia treatment further enhances BDL-induced HSC markers in vivo. FIG. 5A shows that plasma levels of ammonia are significant upregulated in BDL and AAs-fed BDL animals in comparison to sham operated rats (*P<0.05 and P<0.01 vs Sham). OP treatment reduces significant ammonia in BDL-AAs-fed animals in comparison to BDL animals (P<0.01). FIG. 5B shows that hyperammonemia treatment in BDL-induced fibrosis showed an additional significant increase in Myosin IIb, Collagen type I and PDGF-Rβ protein expression in comparison to BDL-induced fibrosis (P<0.01 and *P<0.001). In contrast, treatment with OP, abrogated the strong effect of AAs-fed BDL on all HSC-related activation markers (*P<0.05, P<0.01 and *P<0.001).

DETAILED DESCRIPTION

Figure 1A:
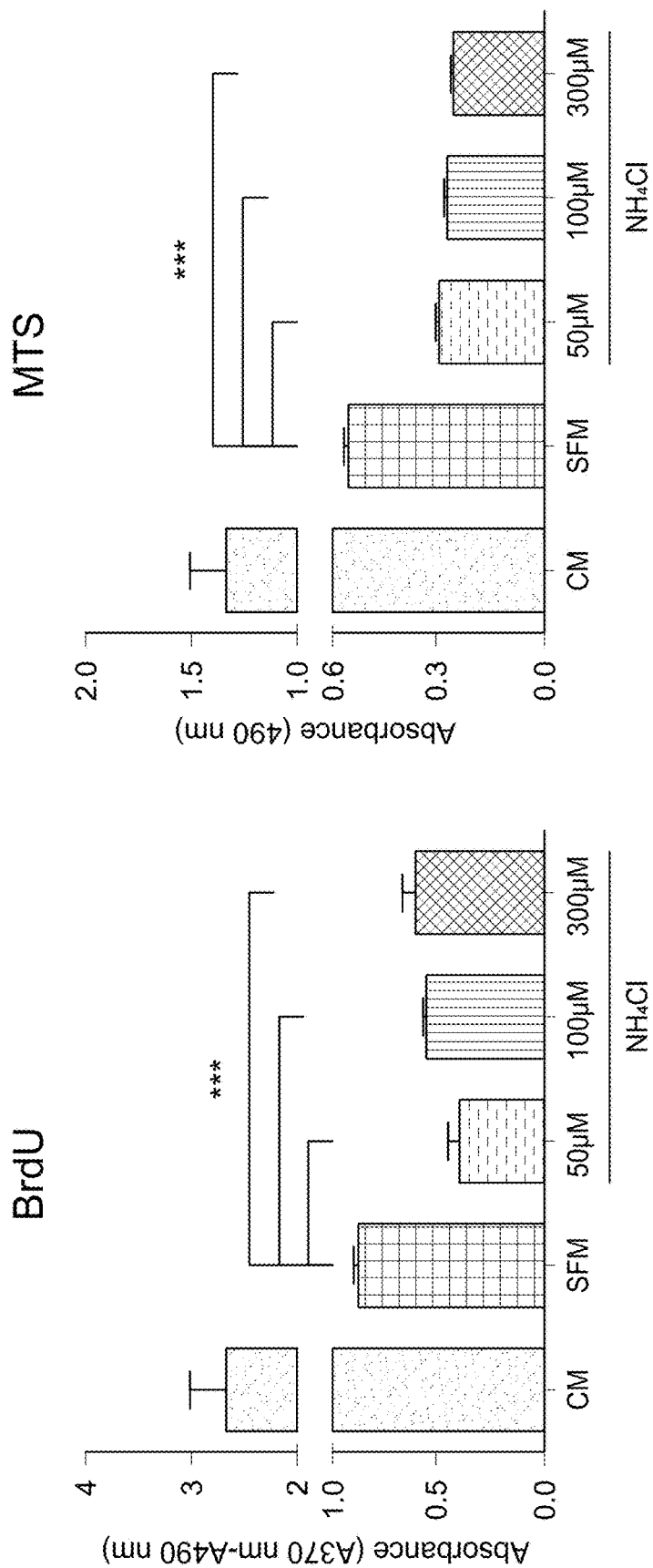
FIGS. 1A-C show ammonia reduces in a dose dependent manner cell proliferation and metabolism in primary human Hepatic Stellate Cells in vitro.

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

Definitions

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional, such as a Medical Doctor (i.e. Doctor of Allopathic medicine or Doctor of Osteopathic medicine) or a Doctor of Veterinary Medicine, to attempt to cure, or at least ameliorate the effects of, a particular disease or disorder or to prevent the disease or disorder from occurring in the first place.

As used herein, "administration" or "administering" refers to a method of giving a dosage of a pharmaceutically active ingredient to a vertebrate.

As used herein, a "unit dosage" refers to an amount of therapeutic agent administered to a patient in a single dose.

As used herein, a "daily dosage" refers to the total amount of therapeutic agent administered to a patient in a day.

As used herein, "therapeutically effective amount" or "pharmaceutically effective amount" is meant an amount of therapeutic agent, which has a therapeutic effect. The dosages of a pharmaceutically active ingredient which are useful in treatment are therapeutically effective amounts. Thus, as used herein, a therapeutically effective amount means those amounts of therapeutic agent which produce the desired therapeutic effect as judged by clinical trial results and/or model animal studies.

As used herein, a "therapeutic effect" relieves, to some extent, one or more of the symptoms of a disease or disorder. For example, a therapeutic effect may be observed by a reduction of the subjective discomfort that is communicated by a subject (e.g., reduced discomfort noted in self-administered patient questionnaire).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Abbreviations

BDL=bile duct ligation.
 OP=ornithine, phenylacetate
 OTC=ornithine transcarbamylase
 GS=glutamine synthetase
 HSC=hepatic stellate cell Ammonia-Lowering Therapies Disclosed herein are various ammonia-lowering therapies that can be used to reduce the ammonia level in a subject. For example, one or more ammonia-lowering agents can be used in the therapy to reduce the ammonia level in the subject. As used herein, the term "ammonia-lowering agent" refers to a substance that can be used to lower the ammonia level in a subject. The mechanism by which the ammonia-lowering agent lowers the ammonia level can vary. For example, the ammonia-lowering agent may lower the ammonia level in a subject by reducing the generation of ammonia in the subject, or by absorbing the ammonia in the subject, or drawing ammonia into the colon and removing ammonia through a laxative effect, or any combination thereof. In some embodiments, the ammonia level in the subject can be the level of ammonia in the blood (e.g., plasma) of the subject. In some embodiments, the ammonia-lowering therapy comprises administering one or more ammonia-lowering agents to the subject.

Non-limiting examples of ammonia-lowering agents include, or comprise, magnesium phosphate product (MGP), glycerol phenylbutyrate (GPB), sodium phenylacetate, sodium phenylbutyrate (NaPBA), glutamine, sodium benzoate, chlorophyll, L-arabinose, laxatives, antibiotics, ornithine in combination with at least one of phenylacetate and phenylbutyrate, and any combination thereof. The ammonia-lowering agents can be present, for example, in a pharmaceutical composition, a nutraceutical composition, a probiotic composition, or any combination thereof. Laxatives are substances that can loosen stools and increase bowel movements. Laxatives can be used to lower ammonia levels in gastrointestinal tract of a subject, for example by altering bacterial flora in the subject's gastrointestinal tract and making few organisms available to produce ammonia. Examples of laxatives include, but are not limited to, lactulose.

The ammonia lowering agent can be, or comprises, one or more antibiotics. For example, the ammonia lowering agent can be administered by the oral route to allow the antibiotic(s) to act in the gastrointestinal tract. Without being bounded by any particular theory, it is believed that the antibiotic(s) can reduce ammonia-producing bacteria from the intestine to reduce the ammonia level in the subject. Non-limiting examples of the antibiotics include neomycin, vancomycin and rifaximin (Xifaxan).

In some embodiments, different ammonia lowering agents are used in combination to reduce the ammonia level in the subject. For example, one or more laxatives and one or more antibiotics can be administered to the subject to reduce ammonia level in the subject.

As another non-limiting example, the ammonia-lower therapy can be, or comprise, adjusting the composition of gut microbiota in the subject. In some embodiments, adjusting the composition of gut microbiota of the subject comprises bacterial transplantation, such as fecal transplantation. In some embodiments, adjusting the composition of gut microbiota in the subject comprises increasing the level of one or more bacterial species lacking or having low urase activity in the gut microbiota of the subject. In some embodiments, adjusting the composition of gut microbiota in the subject comprises replacing the native gut microbiota of the subject with a composition having high level of one or more bacterial species lacking or having low urase activity. In some embodiments, adjusting the composition of gut microbiota in the subject comprise administering to the subject a composition comprising one or more bacterial species lacking or having low urase activity. Examples of the bacteria lacking or having low urase activity include, but are not limited to, Parabacteroides, Lachnospiraceae, Ruminococcaceae, Eubacterium, Mucispirillum, Lactobacillus, and Clostridium. In some embodiments, the bacteria lacking or having lower urease activity is Clostridia, Mucispirillum schaedleri, Parabacteroides, Lactobacilli, or any combination thereof. In some embodiments, the ammonia-lowering therapy comprises transplanting Schaedler flora (ASF), which consists of 8 murine gut commensal bacterial strains that were assembled in the 1970s and standardized by the National Cancer Institute in 1978 (Dewhirst et al., Appl. Environ Microbiol. 1999; 65(8):3287-3292, to the subject. Without being limited by any particular theory, it is believed that bacterial urease converts host-derived urea to ammonia and carbon dioxide, contributing to hyperammonemia and gut microbiota having no or reduced urease activity can reduce ammonia production and thus ammonia level in the subject.

In addition, the ammonia-lower therapy can be, or comprise, gene therapy to correct gene defects that contribute to hyperammonenia in the subject. For example, hyperammonemia can be caused by defects in genes encoding enzymes involved in the urea cycle, including but not limited to, Ornithine Transcarbamylase (OTC) gene, Carbamyl Phosphate Synthetase (CPS1) gene, Argininosuccinic Acid Synthetase (AAS), Argininosuccinate Lyase (ASL), and Arginase (AG). Hyperammonemia can also be caused by defects in cystathione beta synthase (CBS) gene and glutamine synthetase gene. The gene therapy can be performed by methods known in the art. For example, recombinant viral vectors (e.g., adeno-associated viral vectors and baculovius vectors) can be used to deliver (e.g., targeted delivery to liver cells) the missing gene(s) to the subject to reduce the ammonia level in the subject. See e.g., Torres-Vega et al. Gene Therapy (2015) 22, 58-64 (the entire content of which is incorporated herein by reference). In some embodiments, AAV vectors comprising the intact OTC gene are administered into a subject in need thereof to reduce the ammonia level in the subject. In some embodiments, AAV vectors comprising the intact glutamine synthetase gene are administered into a subject in need thereof to reduce the ammonia level in the subject.

Treatment and Prevention of Diseases Associated with HSC Activation

Hepatic stellate cells (HSCs) are liver-specific mesenchymal cells that play important roles in liver physiology and fibrogenesis and maintaining architectural integrity of the liver. HSCs are generally located in the space of Disse and maintain close interactions with sinusoidal endothelial cells and hepatic epithelial cells. HSCs orchestrate many important functions in the liver and their dysfunction is associated with various pathological conditions. HSCs can impact the differentiation, proliferation, and morphogenesis of other hepatic cell types during liver development and regeneration.

In normal liver, HSCs are in a quiescent state. HSCs can change into an activated state when the liver is damaged. For example, following acute or chronic liver injury, HSCs undergo phenotypic transformation from "quiescent" (non-proliferating and non-contractile) to "activated" (promitogenic, profibrogenic, and proinflammatory Myofibroblasts-like) cells. Moreover, during the process of activation, HSCs become highly contractile and have the necessary machinery to contract or relax in response to a number of vasoactive substances/stimuli. Activated HSCs can produce a wide array of cytokines and chemokines which may directly enhance the proliferation of liver progenitor cells and hepatocytes. HSCs are involved in, for example, fibrosis and liver cancer development. HSC activation can lead to various diseases, conditions and symptoms, including but not limited to, non-alcoholic fatty liver disease (NAFLD), fibrotic conditions (for example liver fibrosis), liver cancer, and any combination thereof. Non-limiting examples of liver cancer include hepatocellular carcinoma (HCC) and hepatoblastoma. In some embodiments, the methods of treating and/or preventing diseases associated with HSC activation comprise identifying a subject suffering from or at the risk of developing a disease associated with HSC activation. In some embodiments, the disease associated with HSC activation can be NAFLD, liver fibrosis, liver cancer, or any combination thereof.

NAFLD refers to a group of conditions where there is accumulation of excess fat in the liver of people who drink little or no alcohol. NFALD is a common liver disorder in developed countries. The most common form of NAFLD is a non-serious condition called fatty liver. NAFLD occurs when fat is deposited (steatosis) in the liver. Although having fat in the liver is not normal, by itself it probably does not damage the liver. NAFLD is a common cause of fibrosis. NAFLD is sometimes suspected in an overweight or obese person who is found to have mild elevations in their liver tests during a routine blood testing or incidentally detected on radiologic investigations such as abdominal ultrasound or CT scan.

Non-alcoholic steatohepatitis (NASH) is a more serious form of NAFLD. In NASH, fat accumulation is associated with liver cell inflammation and different degrees of scarring. NASH is a potentially serious condition that may lead to severe liver scarring and cirrhosis. Without being bound by any particular theory, it is believed that NASH is associated with reduced expression and function of ornithine transcarbamoylase (OTC, also called ornithine carbamoyltransferase) in humans and rodents. For example, in experimental NASH, gene and protein expression of the mitochondrial urea cycle enzyme ornithine transcarbamylase (OTC) is reduced significantly, resulting in functional reduction in the in vivo capacity for ureagenesis, which results in hyperammonemia. In patients with biopsy-proven NASH, plasma ammonia levels are increased significantly more than in patients with simple steatosis. In mammals, the OTC enzyme is part of the urea cycle. In a mammal deficient in OTC, ammonia level will build up, which can cause hyperammonemia and subsequently neurological problems.

It is disclosed for the first time in the present disclosure that ammonia produces marked morphological and functional changes in human HSCs and in vivo in bile duct ligated rats (for example, oxidative stress, increased cytokines, expression of activation markers, alterations in the secretion of matrix proteins, and severe morphological disruption). Without being bound by any particular theory, it is believed that hyperammonia can activate HSCs in vivo and in vitro, which may favor the progression of NAFLD (e.g., NASH) and fibrosis. As described herein, a reduction in ammonia level in a subject can prevent the activation of HSCs in the subject and reduces, for example, diseases associated with HSC activation.

Some embodiments described herein provide methods of treating a disease associated with HSC activation in a subject in need by performing on the subject an ammonia-lowering therapy. Some embodiments described herein provide methods of delaying the onset or progression of a disease associated with HSC activation in a subject in need by performing on the subject an ammonia-lowering therapy. In some embodiments, performing the ammonia-lowering therapy comprises administering an ammonia-lowering agent to the subject. In some embodiments, the ammonia-lowering agent is, or comprises, magnesium phosphate product (MGP), glycerol phenylbutyrate (GPB), sodium phenylacetate, sodium phenylbutyrate (NaPBA), glutamine, sodium benzoate, L-arabinose, a laxative, an antibiotic, ornithine in combination with at least one of phenylacetate and phenylbutyrate, or any combination thereof. In some embodiments, the methods comprise co-administering to the subject ornithine in combination with phenylacetate and/or phenylbutyrate. In some embodiments, the disease associated with HSC activation is NAFLD, for example NASH or steatosis. In some embodiments, the disease associated with HSC activation is liver cancer, for example HCC or hepatoblastoma. In some embodiments, the disease associated with HSC activation is a fibrotic condition, for example liver fibrosis. In some embodiments, the subject suffering from liver cancer and/or the fibrotic condition can suffer from NAFLD as well. In some embodiments, two or more ammonia-lowering agents are co-administered to the subject. In some embodiments, one or more ammonia-lowering agents are co-administered with another pharmaceutically active ingredient to the subject. In some embodiments, the composition of gut microbiota in the subject is adjusted to treat a disease associated with HSC activation. In some embodiments, gene therapy is used as the ammonia-lowering therapy to treat a disease associated with HSC activation.

Also disclosed herein are methods of preventing NAFLD by performing an ammonia-lowering therapy on a subject in need thereof. In some embodiments, performing the ammonia-lowering therapy comprise administering an ammonia-lowering agent to the subject. Any of the ammonia-lowering agents disclosed herein can be used in the methods, including but not limited to, magnesium phosphate product (MGP), glycerol phenylbutyrate (GPB), sodium phenylacetate, sodium phenylbutyrate (NaPBA), glutamine, sodium benzoate, L-arabinose, laxatives, antibiotics, ornithine in combination with at least one of phenylacetate and phenylbutyrate, and any combination thereof. In some embodiments, the methods comprise co-administering to the subject ornithine in combination with phenylacetate and/or phenylbutyrate. In some embodiments, the composition of gut microbiota in the subject is adjusted to prevent NAFLD. In some embodiments, gene therapy is used as the ammonia-lowering therapy to prevent NAFLD.

Some embodiments described herein provide methods of treating a fibrotic condition by performing an ammonia-lowering therapy on a subject in need thereof. The ammonia-lowering therapy can comprise, in some embodiments, co-administering to a subject in need thereof an ammonia-lowering agent, such as ornithine in combination with phenylacetate and/or phenylbutyrate. Some such embodiments include therapeutic treatment. Other embodiments include prophylactic treatment. As used herein, a "fibrotic condition" refers to a condition, disease or disorder that is characterized by dysregulated proliferation or activity of fibroblasts and/or abnormal accumulation of fibronectin and/or pathologic or excessive accumulation of collagenous tissue. Typically, any such disease, disorder or condition is amenable to treatment by administration of a compound having anti-fibrotic activity. Fibrotic disorders include, but are not limited to, liver fibrosis (e.g., hepatic fibrosis associated with chronic active hepatitis). Thus, some embodiments include methods of treating liver fibrosis by co-administering to a subject in need thereof ornithine in combination with phenylacetate and/or phenylbutyrate. Some embodiments include identifying a subject as having or at risk for developing a fibrotic condition (e.g., liver fibrosis) prior to administering the ornithine in combination with phenylacetate and/or phenylbutyrate.

By "co-administration," it is meant that the two or more agents may be found in the patient's bloodstream at the same time, regardless of when or how they are actually administered. In some embodiments, the agents are administered simultaneously. In one such embodiment, administration in combination is accomplished by combining the agents in a single dosage form. In some embodiments, the agents are administered sequentially. In some embodiments, the agents are administered through the same route, such as orally. In some embodiments, the agents are administered through different routes, such as one being administered orally and another being administered i.v.

As described herein, NASH is associated with reduced expression and function of the urea cycle enzyme, ornithine transcarbamoylase (OTC) level in humans and rodents, which results in hyperammonemia. Without being bound by any particular theory, it is believed that ammonia is elevated in NAFLD and is involved in the progression of NAFLD and liver cancer. In addition, ammonia-lowering agents (e.g., OP) are useful to reduce blood ammonia level in the subject having hyperammonemia, such as the hyperammonemia associated with NASH, and thus prevent, limit, or slow down progression of NAFLD, fibrosis progression in NASH, and the development of liver cancer (e.g., HCC). In some embodiments, the ammonia-lowering agent is useful to reduce blood ammonia level, which treats and delays the onset or progression of NASH.

Some embodiments include treating a fibrotic condition (e.g., liver fibrosis) by performing an ammonia-lowering therapy on a subject in need. For example, the ammonia-lowering therapy can comprise administering to a subject in need an ammonia-lowering agent, for example ornithine in combination with phenylacetate and/or phenylbutyrate. Some such embodiments include therapeutic treatment. Some embodiments include prophylactic treatment. Some embodiments include identifying a subject as having or at risk for developing the fibrotic condition (e.g., liver fibrosis) prior to administering the ammonia-lowering agent.

Some embodiments include methods of treating a liver cancer by performing an ammonia-lowering therapy on a subject in need. For example, the ammonia-lowering therapy can comprise co-administering to a subject in need thereof an ammonia-lowering agent, for example ornithine in combination with phenylacetate and/or phenylbutyrate. Some such embodiments include therapeutic treatment. Some embodiments include prophylactic treatment. Some embodiments include identifying a subject as having or at risk for developing liver cancer prior to administering the ammonia-lowering agent. Some embodiments include treating liver cancer by administering ornithine in combination with phenylacetate and/or phenylbutyrate, for example ornithine phenylacetate, to the subject. The liver cancer can be, for example, HCC or hepatoblastoma.

Ammonia level in a subject can be determined by various conventional methods. For example, ammonia is routinely measured in plasma from a venous (or arterial) blood sample. It can also be measured in whole blood, erythrocytes, saliva, sweat, and urine. Ammonia measurements can be used to diagnose hyperammonemia. Ammonia can be measured by indirect or direct methods. For example, the ammonia can be measured by the change of color of an ammonium indicator, for example the Vitros® (Ortho Diagnostic Ltd.) ammonia measurement which utilizes bromophenol blue. As another example, an $NH_4^+$-selective membrane which is typically based on a mixture of antibiotics nonatin and monoactin can also be used to measure ammonia level. In some embodiments, the methods disclosed herein comprise determining the ammonia level in the subject prior to and/or after administration of the ammonia-lowering agent. In some embodiments, the ammonia level in the subject is monitored throughout the period in which the subject is receiving the treatment by ammonia-lowering agent. Reduction in ammonia levels in vivo can reduce inflammation (NFκB), oxidative stress and αSMA expression, and increase in nitric oxide synthase (eNOS) activity and function.

Salts

In some embodiments, the ammonia-lowering agents (such as ornithine in combination with phenylacetate and/or phenylbutyrate) are administered as pharmaceutically acceptable salts. The term "pharmaceutically acceptable salt" refers to salts that retain the biological effectiveness and properties of a compound and, which are not biologically or otherwise undesirable for use in a pharmaceutical. In many cases, the ammonia-lowering agents disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable salts can also be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

In some embodiments, ornithine is administered as the ornithine HCl salt. In some embodiments, phenylacetate or phenylbutyrate is administered as their sodium salts. In some embodiments, ornithine and phenylacetate or phenylbutyrate are administered as salts of each other (e.g., ornithine phenylacetate).

Pharmaceutical Compositions and Routes of Administration

The ammonia-lowering agent (such as ornithine in combination with phenylacetate and/or phenylbutyrate) can be formulated for administration with a pharmaceutically acceptable carrier or diluent. The ammonia-lowering agent can, in some embodiments, be formulated as a medicament with a standard pharmaceutically acceptable carrier(s) and/or excipient(s) as is routine in the pharmaceutical art. The exact nature of the formulation will depend upon several factors including the desired route of administration. For example, the ammonia-lowering agent (for example, ornithine and the phenylacetate and/or phenybutyrate) can be formulated for oral, intravenous, intragastric, intravascular or intraperitoneal administration. Standard pharmaceutical formulation techniques may be used, such as those disclosed in Remington's The Science and Practice of Pharmacy, 21st Ed., Lippincott Williams & Wilkins (2005), incorporated herein by reference in its entirety.

The ornithine (e.g., L-ornithine) and phenylacetate or phenylbutyrate may be administered separately or in a single dosage form. In some embodiments, the combination is administered as the ornithine phenylacetate salt or as a solution of the ornithine phenylacetate salt.

Different forms of composition of ornithine in combination with at least one of phenylacetate (or phenyl acetate salts) and phenylbutyrate have been described in U.S. Patent Publication Nos. US2008/0119554 and US2010/0280119, which are hereby incorporated by reference in their entireties. In some embodiments, ornithine and phenylacetate is present and/or administered as ornithine phenyl acetate or physiologically acceptable salt thereof. In some embodiments, ornithine is present and/or administered as a free monomeric amino acid or physiologically acceptable salt thereof. In some embodiments, at least one of phenylacetate and phenylbutyrate is present and/or administered as a sodium phenylacetate or sodium phenylbutyrate. In some embodiments, a physiologically acceptable salt of ornithine and a physiologically acceptable salt of at least one of phenylacetate and phenylbutyrate are administered to the subject.

As disclosed herein, the ornithine and the phenylacetate and/or phenylbutyrate can be formulated for administration in a pharmaceutical composition comprising a physiologically acceptable surface active agents, carriers, diluents, excipients, smoothing agents, suspension agents, film forming substances, coating assistants, or a combination thereof. In some embodiments, the ornithine and the phenylacetate and/or phenylbutyrate are formulated for administration with a pharmaceutically acceptable carrier or diluent. The ornithine and the phenylacetate and/or phenylbutyrate can be formulated as a medicament with a standard pharmaceutically acceptable carrier(s) and/or excipient(s) as is routine in the pharmaceutical art. The exact nature of the formulation will depend upon several factors including the desired route of administration. Typically, ornithine and the phenylacetate and/or phenylbutyrate are formulated for oral, intravenous, intragastric, intravascular or intraperitoneal administration. Standard pharmaceutical formulation techniques may be used, such as those disclosed in Remington's The Science and Practice of Pharmacy, 21st Ed., Lippincott Williams & Wilkins (2005), incorporated herein by reference in its entirety.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, and granules. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual, buccal and nasal dosage forms. Such compositions typically comprise one or more soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one or more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 0.1 mg/kg and 4000 mg/kg body weight, for example between about 1 mg/kg and 1600 mg/kg body weight. Alternatively dosages may be based and calculated upon the surface area of the patient, as understood by those of skill in the art.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The compound or combination of compounds disclosed herein may be administered orally or via injection at a dose from 0.1 mg/kg to 4000 mg/kg of the patient's body weight per day. The dose range for adult humans is generally from 1 g to 100 g/day. Tablets or other forms of presentation provided in discrete units may conveniently contain an amount of the compound or combination of compounds disclosed herein which is effective at such dosage or as a multiple of the same, for instance, units containing 1 g to 60 g (for example, from about 5 g to 20 g, from about 10 g to 50 g, from about 20 g to 40 g, or from about 25 g to 35 g). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. A typical dose of the ammonia-lowering agent (for example, of ornithine, or of phenylacetate or phenylbutyrate) can be from 0.02 g to 1.25 g per kg of body weight, for example from 0.1 g to 0.5 g per kg of body weight, depending on such parameters. In some embodiments, a dosage of the ammonia-lowering agent can be from 1 g to 100 g, for example, from 10 g to 80 g, from 15 g to 60 g, from 20 g to 40 g, or from 25 g to 35 g. In some embodiments, the ornithine and phenylacetate/phenylbutyrate can be administered in a weight ratio from 10:1 to 1:10, for example, from 5:1 to 1:5, from 4:1 to 1:4, from 3:1 to 1:3, from 2:1 to 1:2, or about 1:1. A physician will be able to determine the required dosage of the ammonia-lowering agent (for example, ornithine and of phenylacetate or phenylbutyrate) for any particular subject.

The exact formulation, route of administration and dosage for the pharmaceutical compositions of the compound or combination of compounds disclosed herein can be chosen by the individual physician in view of the patient's condition. (See, e.g., Fingl et al. 1975, in "The Pharmacological Basis of Therapeutics," which is hereby incorporated herein by reference, with particular reference to Ch. 1). Typically, the dose range of the composition administered to the patient can be from about 0.1 to about 4000 mg/kg of the patient's body weight. The dosage may be a single one or a series of two or more given in the course of one or more days, as is needed by the patient. In instances where human dosages for compounds have been established for at least some condition, the present disclosure will use those same dosages, or dosages that are between about 0.1% and about 5000%, more preferably between about 25% and about 1000% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. In cases of administration of a pharmaceutically acceptable salt, dosages may be calculated as the free base. In some embodiments, the composition is administered 1 to 4 times per day. Alternatively the compositions of the compound or combination of compounds disclosed herein may be administered by continuous intravenous infusion, preferably at a dose of each active ingredient up to 100 g per day. As will be understood by those of skill in the art, in certain situations it may be necessary to administer the compound disclosed herein in amounts that exceed, or even far exceed, the above-stated, preferred dosage range in order to effectively and aggressively treat particularly aggressive diseases or infections. In some embodiments, the compound or combination of compounds disclosed herein will be administered for a period of continuous therapy, for example for a week or more, or for months or years.

In some embodiments, the dosing regimen of the compound(s) or combination of compounds disclosed herein is administered for a period of time, which time period can be, for example, from at least about 1 week to at least about 4 weeks, from at least about 4 weeks to at least about 8 weeks, from at least about 4 weeks to at least about 12 weeks, from at least about 4 weeks to at least about 16 weeks, or longer. The dosing regimen of the compound(s) or combination of compounds disclosed herein can be administered three times a day, twice a day, daily, every other day, three times a week, every other week, three times per month, once monthly, substantially continuously or continuously.

EXAMPLES

Some aspects of the embodiments of the present application are disclosed in further detail in the following examples, which are not in any way intended to limit the scope of the present disclosure.

Example 1

In Vitro Effect on Primary Human HSCs

Primary human hepatic stellate cells (hHSCs) were cultured. Effects of an $NH_4Cl$ challenge (0.1-10 mM over 24-72 hrs) on hHSC proliferation (BrdU), metabolic activity (MTS assay), viability (Neutral-Red), ultrastructural changes (TEM) and gene/protein expression (q-PCR/Western blot) were studied. To test recovery, ammonia treated cells were replenished with glutamine and in separate experiments, pre-treated with L-methionine-sulfoximine (MSO-GS inhibitor) to determine the importance of glutamine synthetase (GS).

Hyperammonemia in primary hHSCs induced time dependent decreases in proliferation and metabolic activity, whilst inducing cell swelling and a myo-fibroblast-like phenotype even at 50-100 umol/L. Ultrastructurally, ammonia-treated hHSC had dose-dependent intracellular ER enlargement and this was reversible by replenishing the culture with L-glutamine. $NH_3$ inhibition of hHSC proliferation was dependent on GS activity as MSO and hyperammonemia induced cell detachment and prevention of recovery suggesting that glutamine is important for hHSC survival.

These results suggest that hyperammonemia modifies hHSC's and imparts a swollen myofibroblast phenotype, which is reversible upon ammonia reduction. Accordingly, it is anticipated that therapy that reduces ammonia can surprisingly prevent and reverse liver fibrosis.

Example 2

In Vivo Effect in BDL Rats 28-day bile duct ligated (BDL) rats were treated with saline or ornithine phenylacetate for 5 days. Portal pressure was measured at termination and tissues were harvested for studies. BDL rats with hyperammonemia had increased hepatic expression of pro-fibrogenic hHSC-related genes (α-SMA, PDGFb-R, Myosin IIA/IIB and Coll1), low eNOS activity and DDAH-1, and high portal pressure, all of which were corrected by treatment with ornithine phenylacetate.

These results demonstrate that in vivo ammonia lowering with ornithine phenylacetate decreases pro-fibrogenic and activated HSC gene and protein expression. This data supports the use of ornithine phenylacetate in the treatment (including prevention) of liver fibrosis and liver cancer (stellate cell activation can result in liver cancer).

Example 3

Ammonia Modulates Human HSC Activation

This example shows that ammonia produces deleterious morphological and functional effects on HSCs, and ammonia-induced dysfunction of HSCs is reversible using an ammonia-lowering agent OP.

Methods

In this example, primary human HSCs (hHSCs) were isolated and cultured. Proliferation (BrdU), metabolic activity (MTS), morphology (TEM, light- and immunofluorescence microscopy), HSC activation markers, ability to contract, and changes in oxidative status (ROS) were evaluated to identify effects of ammonia challenge (50 μM, 100 μM, 300 μM) over 24-72 hours. Changes in plasma ammonia levels, markers of HSC activation, portal pressure and hepatic eNOS activity were quantified in hyperammonemic BDL animals, and after OP treatment.

In Vitro Studies in Human HSC

Primary hHSCs were isolated from wedge sections of liver tissue, obtained from patients undergoing surgery in the Royal Free Hospital after giving informed consent (EC01.14-RF). Cells were isolated according to Mederacke et al. (Nature Protocols 2015, 10:305-315) with modifications for human liver as described in Rombouts K, Carloni V. Determination and characterization of tetraspanin-associated phosphoinositide-4 kinases in primary and neoplastic liver cells. In: Waugh MG, editor. Lipid Signaling Protocols, 2 ed. New York: Springer Science+Business Media; 2015. p. 203-212). Briefly, 10 g of total human liver tissue was digested with 0.01% Collagenase, 0.05% Pronase and 0.001% DNase I without performing perfusion. The homogenate was filtered through a 100 μm cell strainer and the flow-through was centrifuged at 50×g for 2 minutes at 4° C. After washing the supernatant, gradient centrifugation was performed at 1400×g for 17 minutes at 4° C. using an 11.5% Optiprep gradient. Finally, the interface was collected and washed. Purity of hHSCS was established by detection of CD140b (PDGFRbeta), CD29 (Integrin beta 1) and Cytoglobin (CYGB).

The obtained HSCs were cultured in RPMI supplemented with 20% fetal bovine serum (FBS), GLUTAMAX, nonessential amino acids 1×, 1.0 mM sodium pyruvate, 1× antibiotic-antimycotic (all Life Technologies), referred to as complete HSC medium hereinafter. Experiments described in this study were performed on hHSCs of at least three independent cell preparations between passage 3 and 8.

Cells were seeded (density $26 \times 10^3/cm^2$) under basic serum-rich conditions (CM complete medium) for 24 hours, followed by serum deprivation for another 24 hours (SFM). Exogenous glutamine was removed from the culture medium to avoid uncontrolled generation of ammonia. Specific treatment with $NH_4Cl$ treatments were replaced daily for the duration of the experiment.

Animal Models

All animal experiments were conducted according to the Home Office guidelines under the UK Animals in Scientific Procedures Act 1986 with approval of the ethical committee for animal care of University College London. This study was performed in male Sprague-Dawley rats (Charles River UK, Margate, UK), weighing 220-250 g.

In one experimental model, rats were administered a high protein/ammoniagenic diet (AAs) for 5 days. Furthermore, all rats underwent BDL to induce cirrhosis or a sham operation as described previously.

Study design. (i) In the first protocol, the prior in vitro observations of ammonia-induced effects on HSC cell biology were further explored in vivo. In this experimental protocol, animals underwent BDL surgery and were given 4 weeks to develop liver injury. During the 4th week, BDL animals were randomized into 3 groups: one group contained BDL rats receiving an amino acid-rich (AAs) diet in addition to injection of intraperitoneal (i.p.) saline solution (n=4); a second group received the AAs diet and was treated with an i.p. injection of the ammonia-lowering agent ornithine phenylacetate (OP) 0.3 g/kg twice a day for 5 days (n=4); the third group consisted of BDL rats receiving saline solution i.p. (n=4). In addition to the BDL animals, a further group of sham-operated rats received saline solution (i.p.) (n=4). Animals were sacrificed on the 5th day of treatment.

(ii) In a second protocol, the effect of the ammonia-lowering agent OP on ammonia-induced portal hypertension was investigated. Four weeks after BDL or sham operation, rats were randomized into three groups: sham-operated rats receiving saline (i.p.) (n=18) twice a day for the experimental period of 5 days; BDL rats (n=20) were administered i.p. saline twice a day for 5 days; a further group of BDL rats (n=11) received i.p. injection of OP 0.3 g/kg twice a day for 5 days. Between weeks 4 and 5, following anesthesia (2% isofluorane), rats from each group underwent assessment of mean arterial pressure via isolation and cannulation of the right carotid artery. In addition, portal pressure was measured by direct cannulation of the main portal vein. All measurements were transduced to a Powerlab (4SP) linked to Chart v5.0.1 software. The mean of three readings taken one minute apart was recorded. Liver tissue was harvested and snap-frozen for storage at −80° C. until analyzed.

Statistical Analysis

Results were expressed as mean values±SEM and compared using one-way analysis of variance followed by Dunnet's or Tukey's multiple comparison post hoc tests, where appropriate. P values ≤0.05 were considered significant.

In vivo experimental data were analyzed by t tests and Mann-Whitney U test as appropriate; P<0.05 was considered statistically significant. Results are presented as mean values±SEM using GraphPad Prism software (GraphPad, La Jolla, Calif.)

Results

Figure 1B:
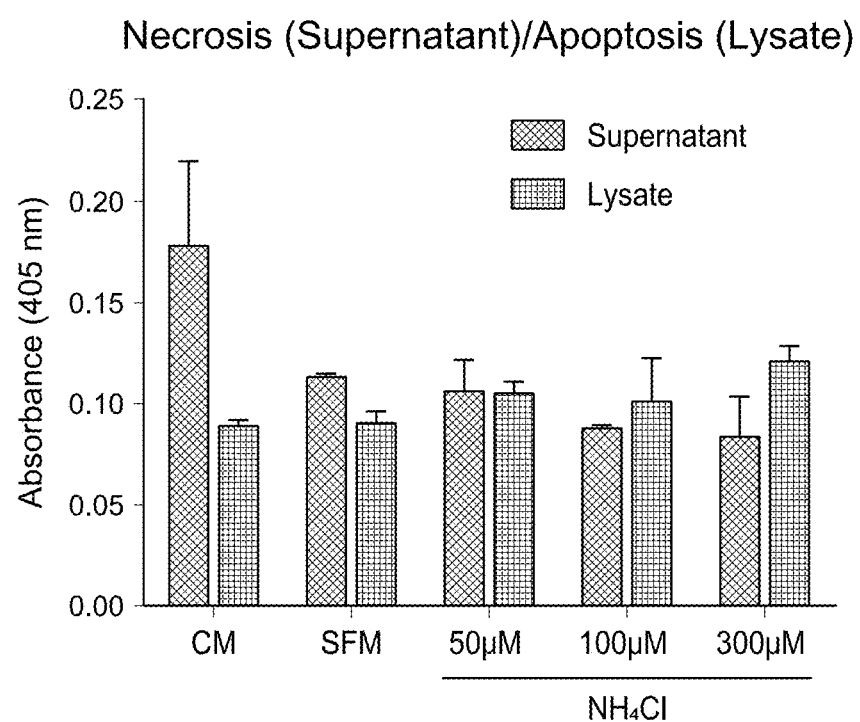
Figure 1C:
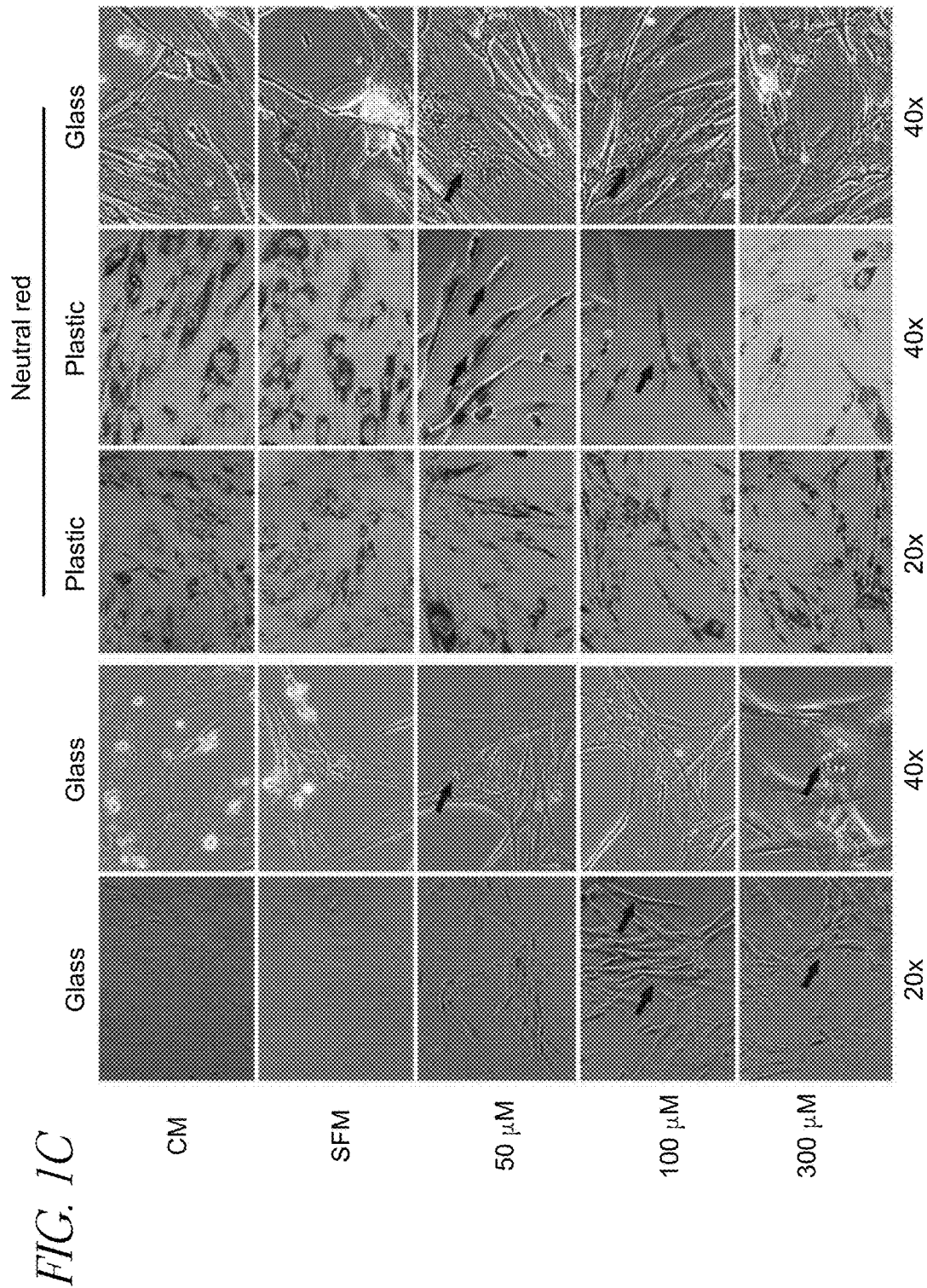

*Ammonia Reduces Cell Proliferation and Metabolism in Human Hepatic Stellate Cells (hHSCs) In Vitro in a Dose Dependent Manner.* hHSCs treated with different concentrations of ammonia for 72 hours showed a significant inhibition in cell proliferation (BrdU assay) and metabolic activity (MTS assay) (FIG. 1A). Furthermore, long term treatment of cells with ammonia did not cause cell death in hHSCs as assessed by deploying the Cell Death Detection ELISA (FIG. 1B). Also, these ammonia-induced effects coincided with strong alterations in cellular morphology in a dose-dependent manner as observed by light microscopy (FIG. 1C). hHSCs, known as myofibroblast-like cells, as shown in complete medium and under serum starvation changed their morphology drastically into a spindle-like fibroblast phenotype, with signs of deregulation of the endo-lysosomal compartment when treated with ammonia as assessed by Neutral Red, a dye retained by the lysosomes (FIG. 1C). It was found that hHSCs express glutamine synthetase (GS) at the mRNA and protein level. Pretreatment of cells with L-Methionine sulfoximine (MSO, a biochemical inhibitor of GS), followed by exposure to ammonia did not further inhibit proliferation and metabolic activity in comparison to MSO treatment only.

Ammonia Induces Alterations in Cytoplasmic Stress, which Coincides with Changes in Cellular Metabolism/Function and Actin Cytoskeleton Architecture.

Figure 2A:
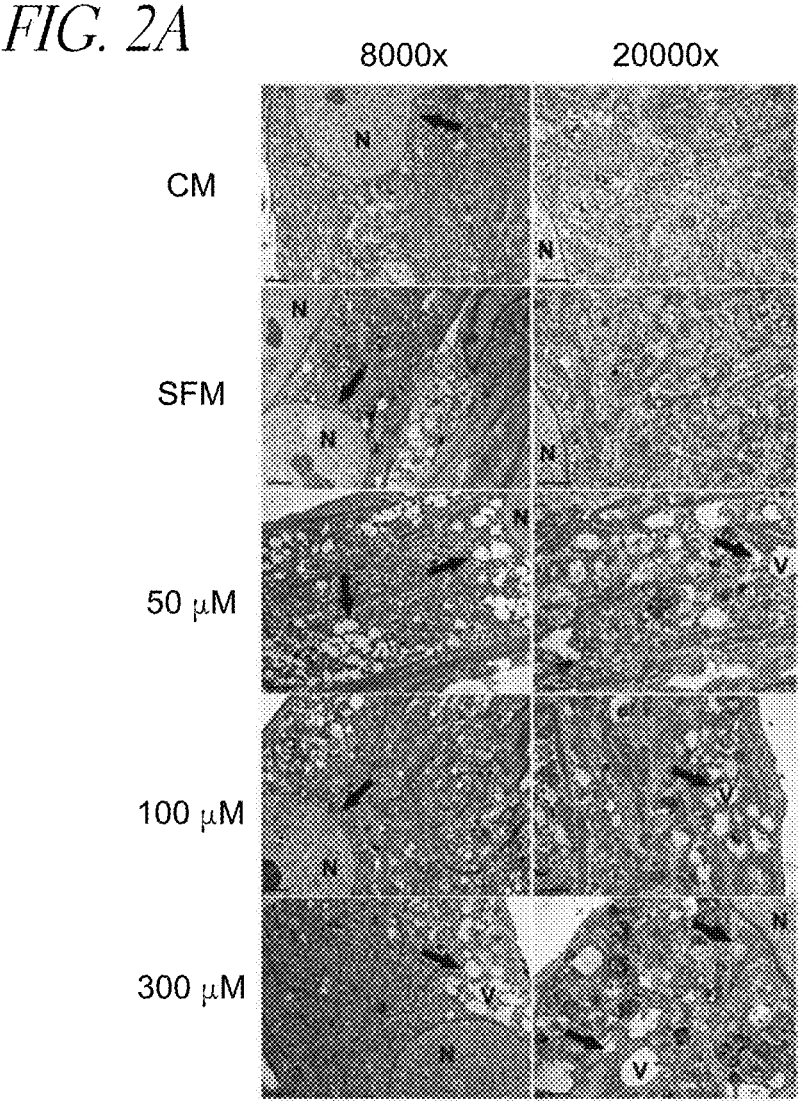
FIGS. 2A-F show ammonia induces alterations in cytoplasmic stress, which coincides with changes in cellular metabolism/function, contraction, and actin cytoskeleton architecture.
Figure 2B:
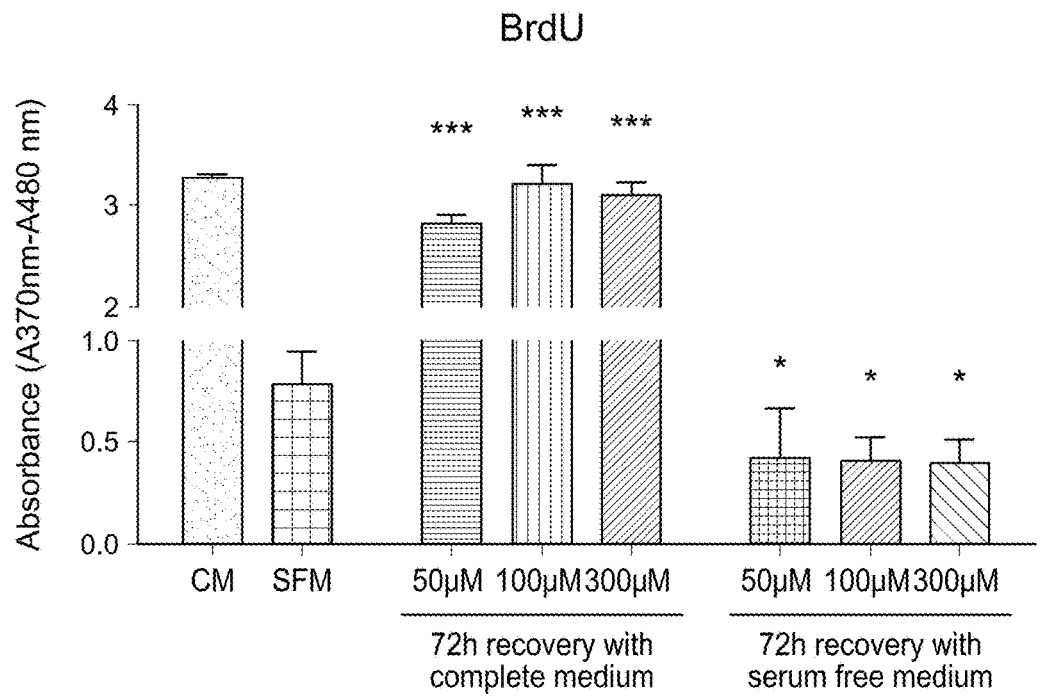
Figure 2B:
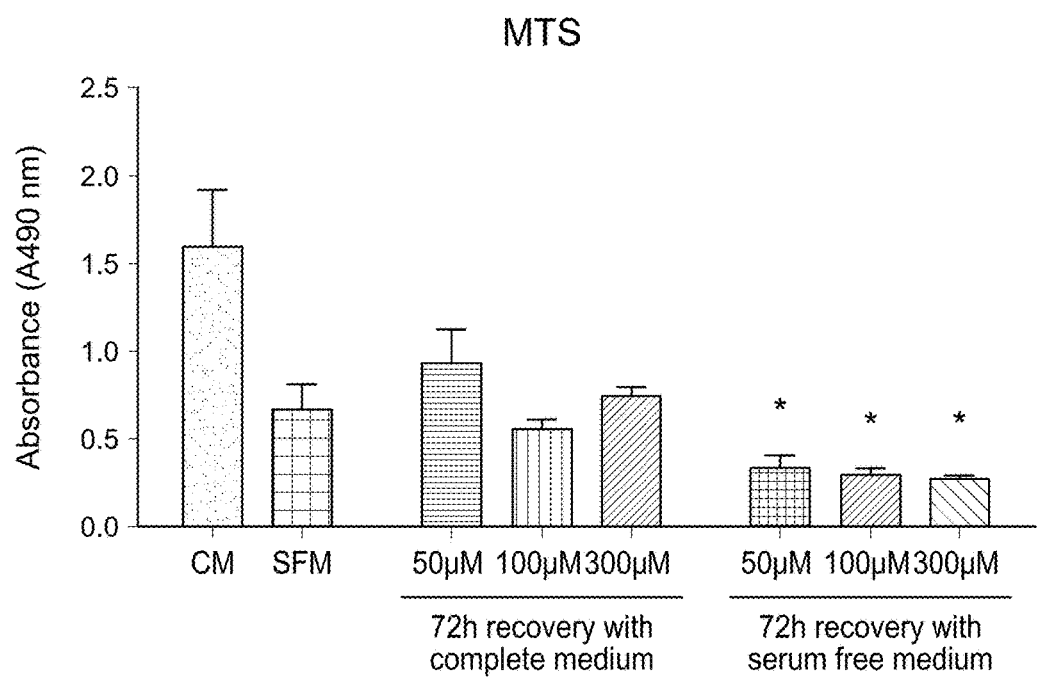
Figure 2C:
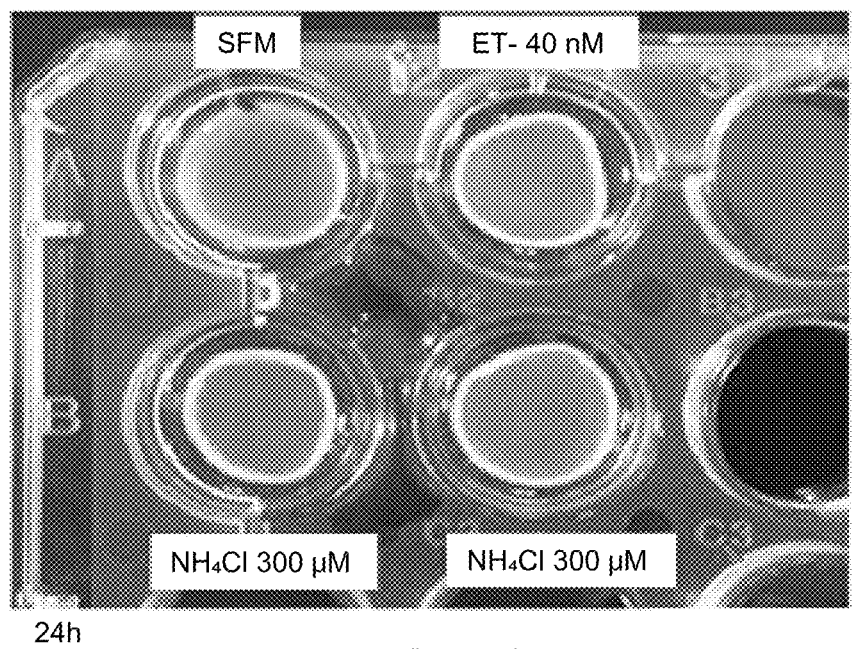
Figure 2D:
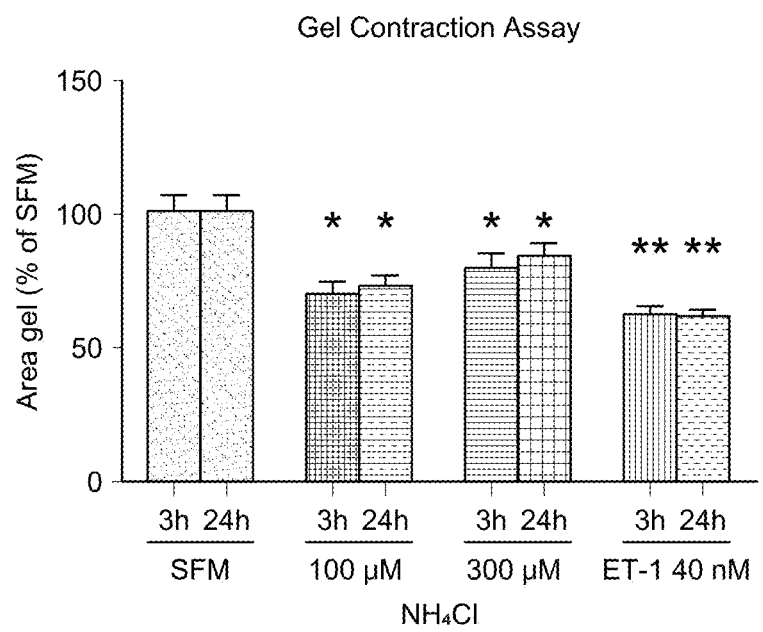
Figure 2E:
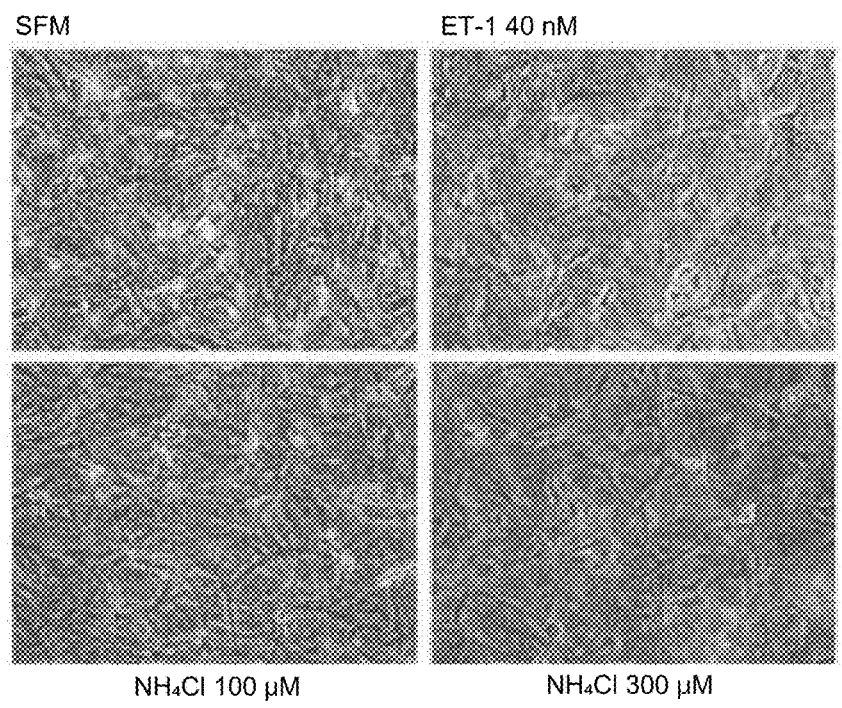
Figure 2E:
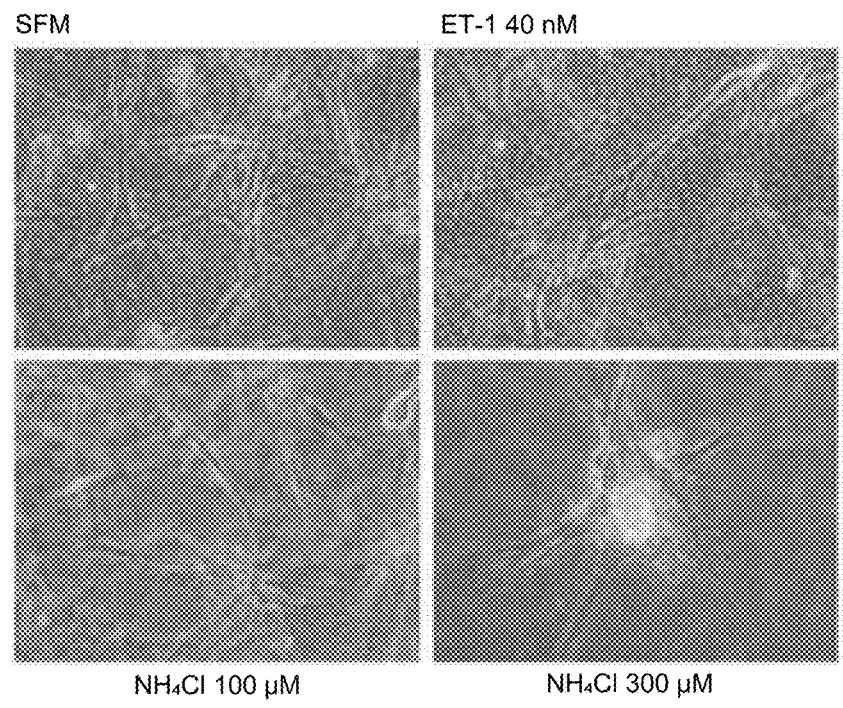
Figure 2F:
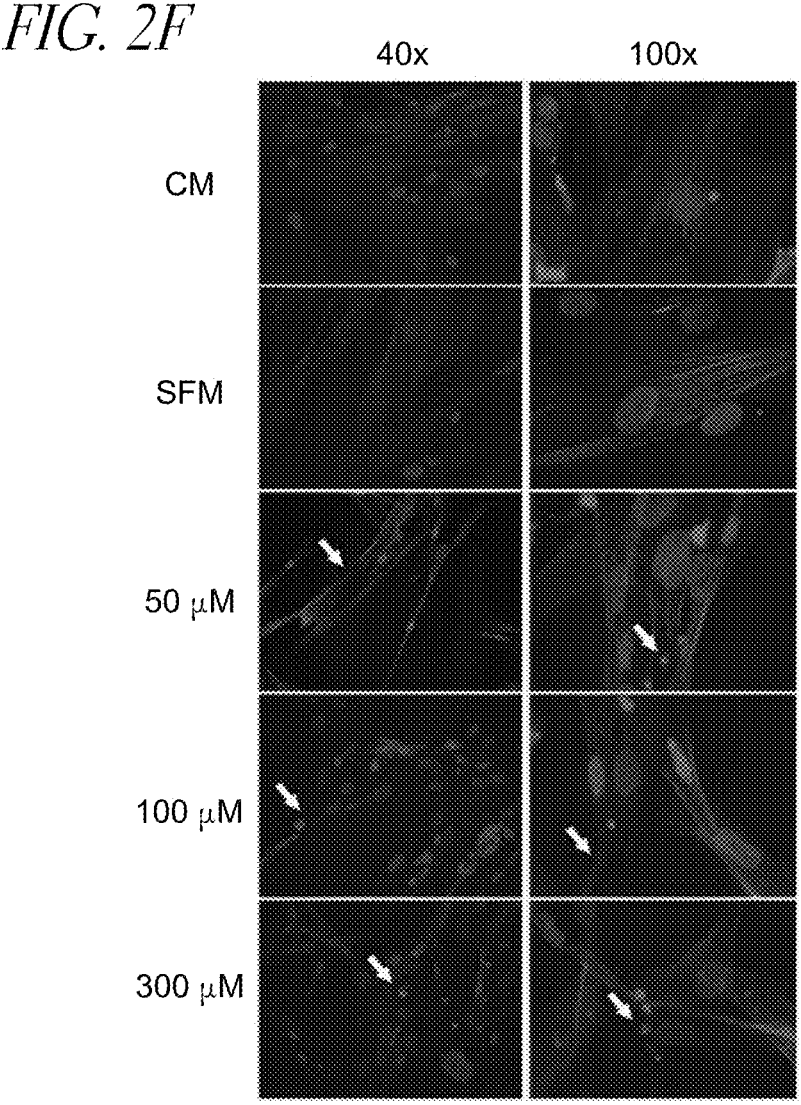

The morphological changes observed by light microscopy were further characterized by performing ultrastructural studies. Ammonia caused a dramatic dose-dependent change in the cytosol and marked presence of translucent vacuoles. Neither mitochondrial alterations nor presence of autophagic structures (characterized by double membranes) were observed (FIG. 2A). It was noted that when ammonia-rich medium was removed and cells were replenished with complete medium both cell proliferation and metabolic activity were restored (FIG. 2B), thus supporting that the observed effect of ammonia is transient. Moreover, ammonia-treated hHSCs cultured on collagen gels showed a significant ability to contract (FIG. 2C, 2D) when compared to control, and this occurred after 3 hours and was sustained after 24 hours of ammonia treatment which coincided with the previously observed morphological changes (FIG. 2E). Furthermore, long-term treatment with ammonia (72 hours) induced a dose-dependent disruption of filamentous actin in the cytoskeleton when TRICT-Phalloidin staining was employed. Re-organization of the F-actin network coincided with the presence of translucent vacuoles in a dose dependent manner (FIG. 2F).

Hyperammonemia Induces ROS Production in hHSC.

Figure 3A:
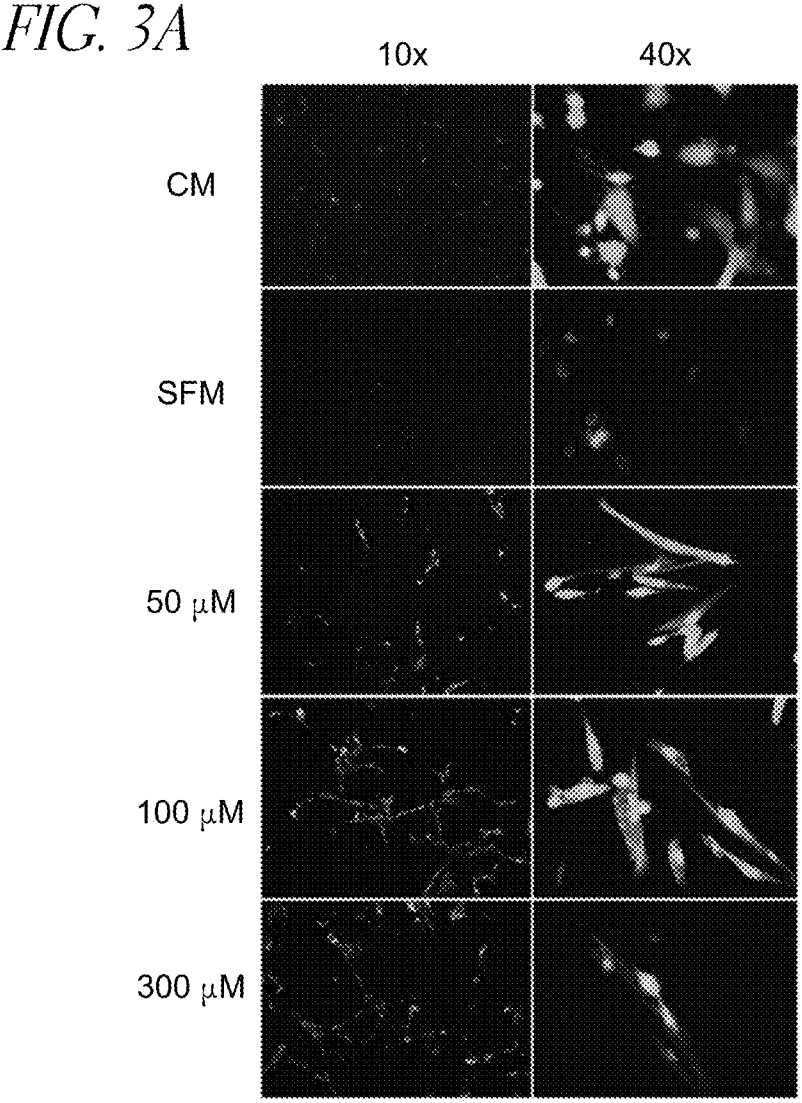
FIGS. 3A-C show ammonia induces ROS production.
Figure 3B:
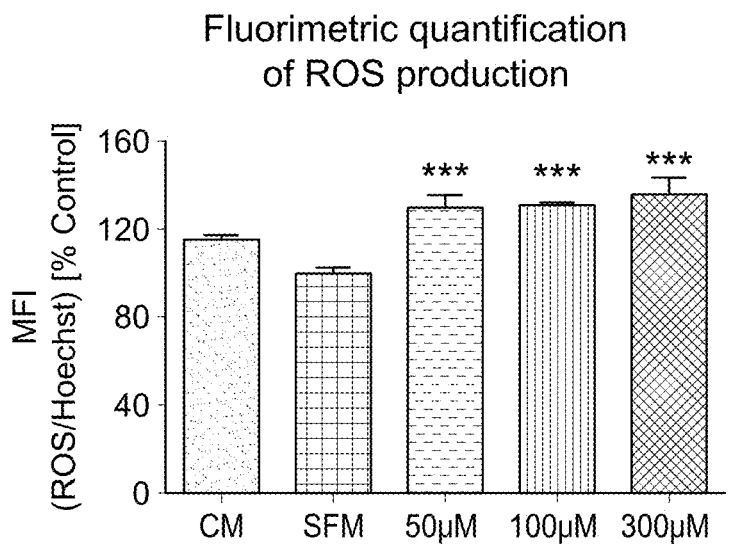
Figure 3C:
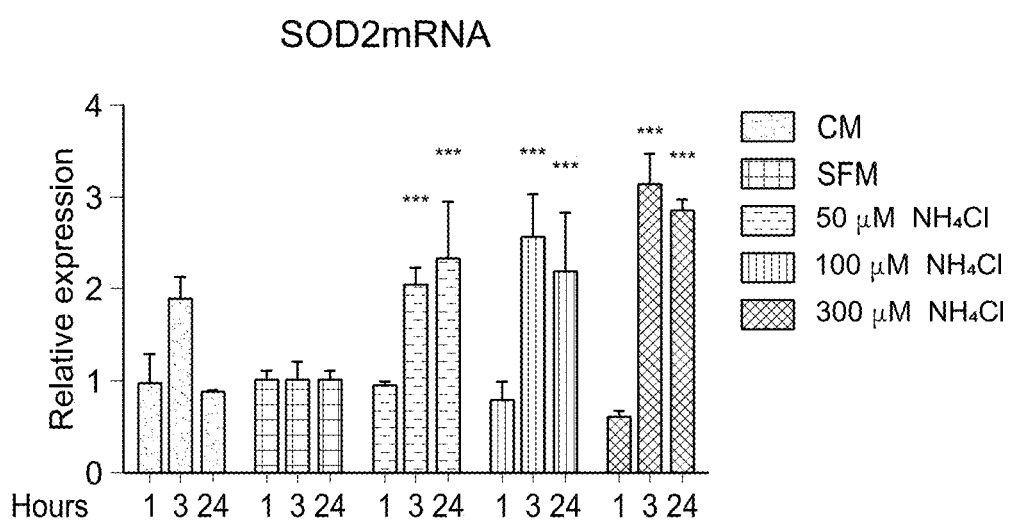
Figure 3D:
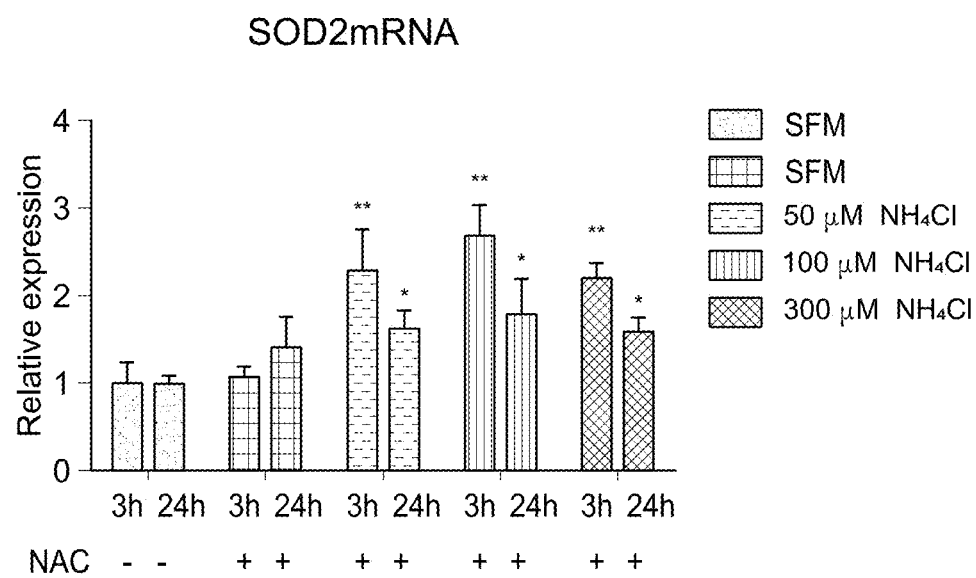
FIG. 3D shows NAC-induced ROS scavenger reduces ammonia-induced SOD2 mRNA expression at 24 hours. Bar graphs show means of 2 independent values±SD. *P<0.05**P<0.01 vs corresponding values of SFM.

Prolonged treatment of cells with ammonia for up to 72 hours showed a gradual development of ROS as detected by the presence of cytosolic carboxy-DCF (FIG. 3A). The development of ammonia-induced ROS production was further quantitatively measured as described in Mookerjee et al., (Gastroenterology, 2007, 132:2533-2541) and confirmed that primary hHSCs treated with ammonia produced significant reactive oxygen species (ROS) (FIG. 3B). Next, cells treated with ammonia for different time points showed a strong increase in mRNA expression of Superoxide dismutase 2 (SOD2) after 3 hours, which was sustained at 24 hours of ammonia treatment (FIG. 3C). Moreover, pre-treatment with N-acetyl cysteine (NAC), a known ROS scavenger, showed no impact on the previously observed increase in SOD2 mRNA expression after 3 hours of ammonia treatment. In contrast, pre-treatment with NAC followed by ammonia treatment for 24 hours, almost completely abolished ammonia-induced SOD2 mRNA expression.

Ammonia Alters the Pro-Fibrogenic/Pro-Inflammatory Profile in hHSCs.

Figure 4A:
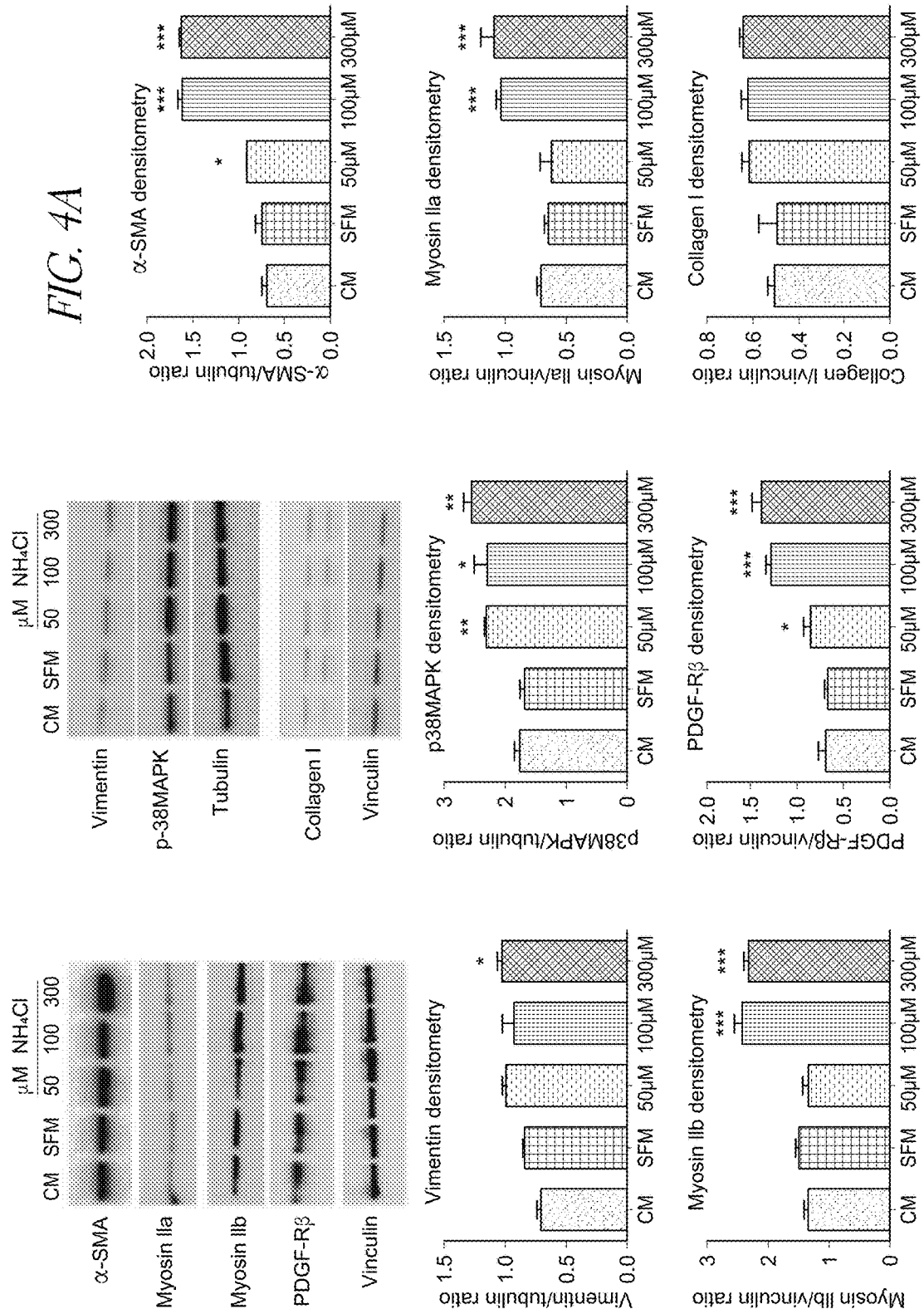
FIGS. 4A-C show ammonia modifies mRNA expression and protein level of several pro-inflammatory and HSC activation markers.
Figure 4B:
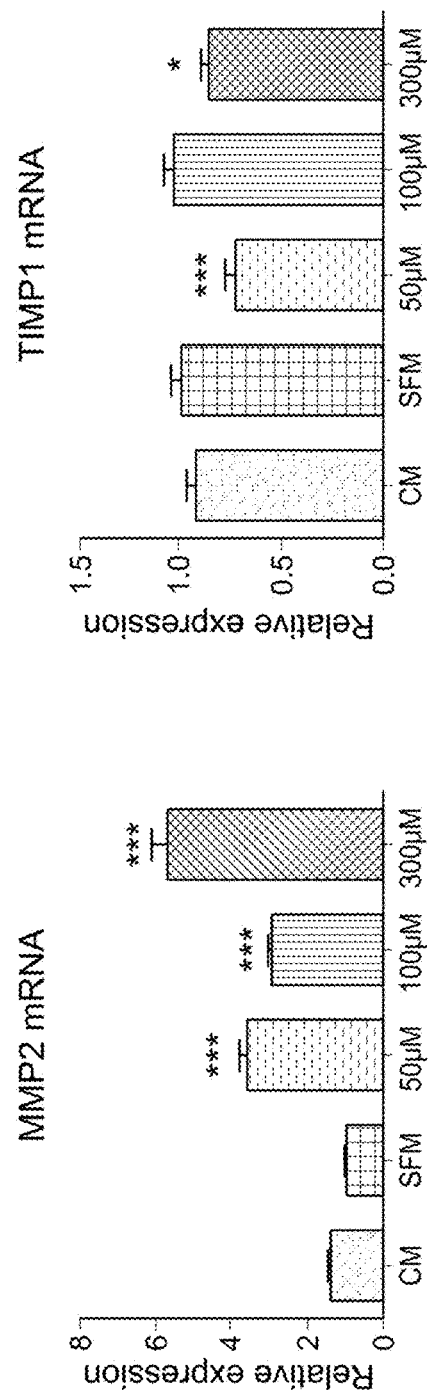
Figure 4C:
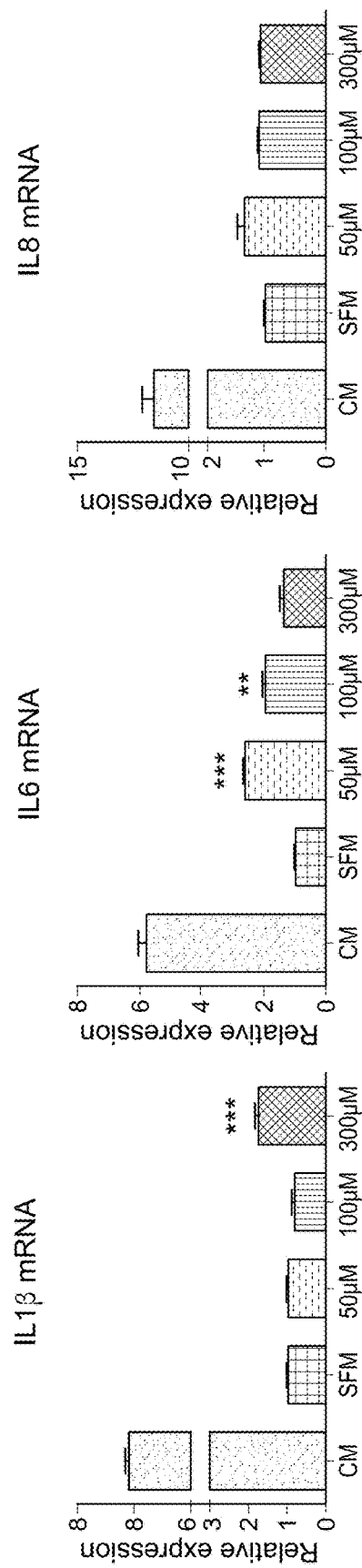

As shown in FIG. 4A, ammonia was shown to significantly increase α-SMA protein expression. At 300 μM ammonia, vimentin (an important intermediate filament) synthesis was increased. Both Myosin IIa (plays an important role in HSC contraction) and Myosin IIb (implicated in HSC activation) were significantly modulated by increasing concentrations of ammonia. A dose-dependent response to ammonia was also observed in P-38 MAPK expression. Furthermore, PDGFR-β, important in HSC cell proliferation, showed a significant up-regulation under influence of ammonia, whereas Collagen type I showed a tendency to increase by ammonia, albeit these effects were not statistically significant (FIG. 4A). Furthermore, ammonia induced a strong and significant up-regulation of MMP2 mRNA expression, whereas mRNA expression of TIMP1 was down-regulated (FIG. 4B). Moreover, pro-inflammatory Interleukin-10 mRNA expression was significantly induced when hHSCs were treated with ammonia 300 μM for 72 hours (FIG. 4C), whereas ammonia at 50 μM and 100 μM doses significantly up-regulated Interleukin 6 mRNA expression level. By contrast, ammonia did not modify Interleukin 8 mRNA expression in HSC (FIG. 4C). These data show that ammonia-induced ROS formation causes alterations in HSC-related activation markers and pro-inflammatory genes.

Bile Duct Ligation and Ammonia Treatment Modifies HSC Cell Biology in Vivo.

Figure 5A:
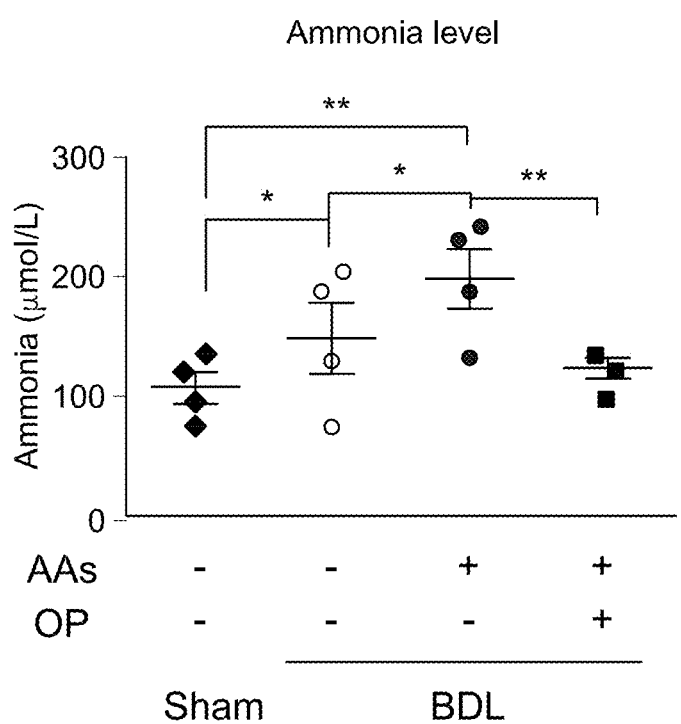

The effect of hyperammonemia on HSC-related signaling pathways in whole liver tissue was investigated. Ammonia concentrations are significantly elevated in BDL rat plasma compared to sham-operated rats (149.3 μmol/L±51.1 vs. 107.4 μmol/L±23.2, P<0.05). Plasma ammonia levels further increased when animals were fed an amino acid-rich (AAs) diet in combination with BDL surgery (199.1 μmol/L±43.6 vs. 149.3 μmol/L±51.1, P<0.05) (FIG. 5A). More importantly, plasma ammonia levels decreased significantly when BDL-AAs-fed animals were treated with OP (123.9 μmol/L±16.1 vs. 199.1 μmol/L μM±43.6, P<0.001) (FIG. 5A).

OP treatment was found to result in a marked decrease in protein expression of HSC-related activation markers (FIG. 5B). More specifically, BDL in combination with hyperammonaemia (AAs diet) showed a significant increase in Myosin IIb, Collagen type I, and PDGF-Rβ protein expression in comparison to BDL. In contrast, treatment with OP abrogated the strong effect of hyperammonemia on BDL rat livers in relation to all HSC-related activation markers tested (FIG. 5B).

The example shows that pathophysiological ammonia concentrations caused significant and reversible changes in cell proliferation, metabolic activity and activation markers of hHSCs in vitro. Ammonia also induced significant alterations in cellular morphology, characterized by cytoplasmic vacuolization, ROS production, hHSC contraction and changes in pro-inflammatory gene expression together with HSC-related activation markers such as α-SMA, myosin IIa, IIb, and PDGF-Rβ. Treatment with an ammonia-reducing agent OP significantly reduced plasma ammonia (BDL 199.1 μmol/L±43.65 vs. BDL+OP 149.27 μmol/L±51.1, P<0.05), which was associated with increased eNOS activity and abrogation of HSC activation markers.

Example 4

OTC Gene Expression and Hepatic Urea Nitrogen Handling are Reduced in NAFLD Animals and Recovers with Dietary Modulation and Reducing Bacterial Translocation This example shows that gene and protein expression of ornithine transcarbamylase (OTC) are altered in animal models of NASH and the alteration is reversible with recovery of animals by restoring the diet and by reducing bacterial translocation. This example also shows that gene expression of OTC is altered in NAFLD patients.

Two animal models of NASH were studied: a) Wistar rats were fed a high-fat, high-cholesterol diet (HFHC) for 10 months and then recovered for 2 months on standard diet, and b) Mice were fed a methionine-choline deficient diet (MCD) for 4 weeks and treated with Yaq-001 (Yaqrit Ltd.), a nanoporous carbon which has been shown to reduce bacterial translocation. In addition, liver biopsies from 16 NAFLD human patients were obtained during bariatric surgery and the OTC gene expression in those liver biopsies was measured.

Figure 6:
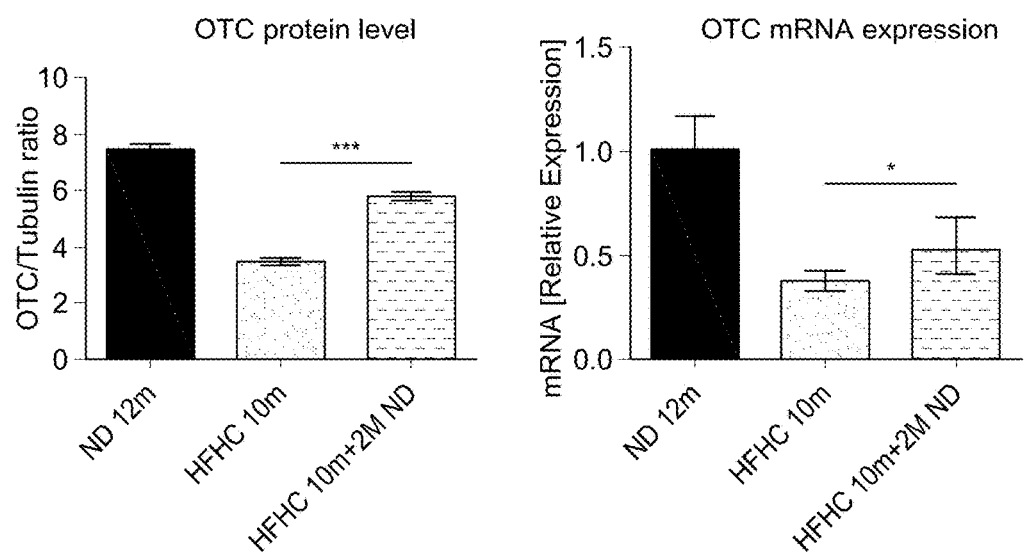
FIG. 6 shows expression of ornithine transcarbamylase (OTC) protein and gene in rats fed a normal and a high-fat high-cholesterol diet for 10 months and recovery for 2 months.
Figure 7:
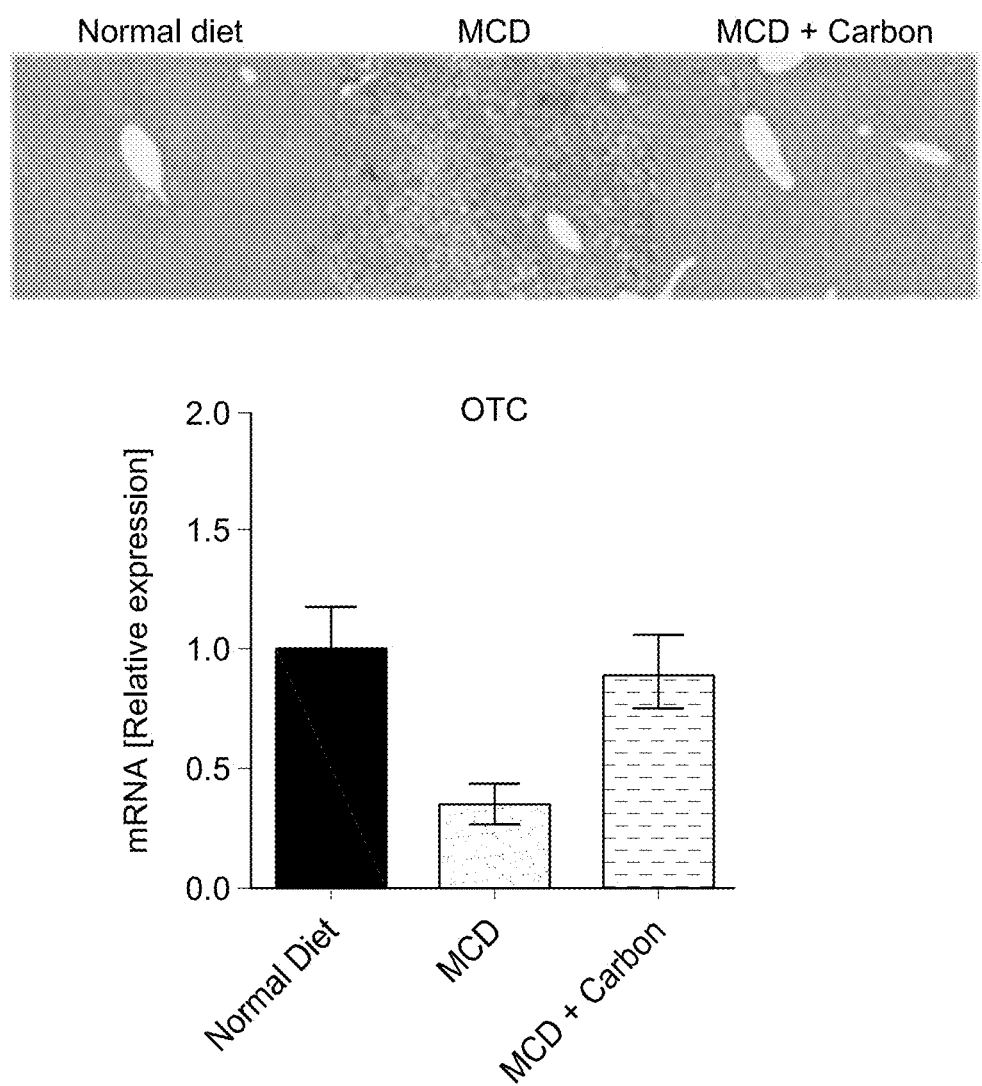
FIG. 7 shows OTC gene expression in mice fed a methionine-choline deficient diet (MCD) for 4 weeks and treated with or without carbon.

In both of the NASH animal models, gene and protein expression of OTC was reduced significantly and the reduction was restored by dietary modulation or reduction in bacterial translation. For example, in the HFHC rats, reversal of NASH by changing the diet to normal chow restored OTC gene expression (0.53 (CI 0.41-0.68) vs. 0.32 (CI 0.28-0.37), P<0.05; controls 1.00 (CI 0.85-1.17)) and OTC protein expression (5.33±0.21 vs. 3.06±0.20, P<0.01; controls 7.41±0.68) (FIG. 6). In the MCD mice, reduction in bacterial translocation prevented development of NASH and restored OTC gene expression (0.89 (CI 0.13-0.16) vs. 0.35 (CI 0.08-0.09), P<0.01; controls 1.00 (CI 0.12-0.17)) suggesting that inflammation in NASH contributes to OTC gene expression (FIG. 7).

Figure 8:
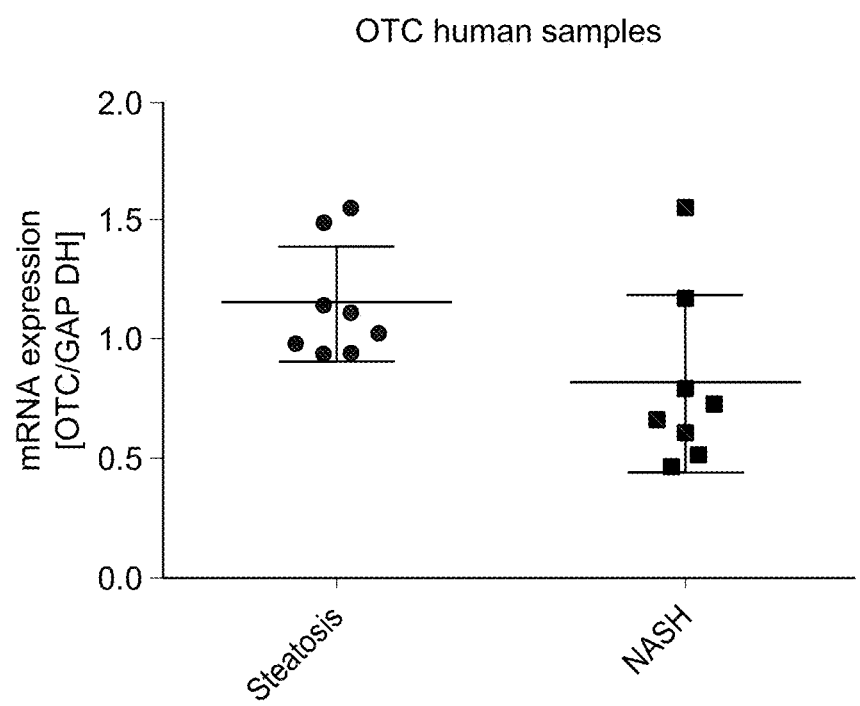
FIG. 8 shows OTC gene expression in NAFLD human patients with simple steatosis or NASH+fibrosis during bariatric surgery.

In the NAFLD patients, those with NASH and fibrosis had significantly lower OTC gene expression than patients with steatosis alone (0.82±0.37 vs. 1.15±0.24, P=0.05) (FIG. 8).

As shown in this example, experimental and human NASH resulted in a reduction in gene expression of the urea cycle enzyme OTC impairing nitrogen homeostasis. The changes were reversible in the animal models of NASH with dietary intervention and also by reducing bacterial translocation. The results shown herein indicate a link between NASH, reduction in gene expression and function of OTC and bacterial translocation. Moreover, ammonia produces morphological changes and activation of HSCs, and OTC reduction can result in hyperammonemia and progression of liver injury and fibrosis. This example supports targeting ammonia and bacterial translocation as treatments for NASH.

Example 5

Hyperammonemia Leads to Disease Progression and Administration of Ammonia-Reducing Agent Reduces Progression of NASH and Fibrosis Two Animal Models are studies in this example: (i) Sprague Dawley rats are subdivided and fed either a diet enriched in High Fat and High Cholesterol (HFHC diet) or a standard diet without high fat and cholesterol content (Standard diet) for up to 16 weeks; and (ii) Rats are fed a High Fat diet supplemented with Fructose (HFD+F diet) for up to 16 weeks.

Interventions study: (i) Prevention therapy—OP are given simultaneously with the fat supplemented diets to the rat;

(ii) Interventional therapy starts 8 weeks after diet-induced NASH to mimic a therapeutic intervention in established NASH rat model. Subgroups are administered OP (0.3 g/kg twice a day, orally) or placebo. In total, 6 experimental groups are investigated: 1) Standard diet+saline; 2) Standard diet+OP (week 1-16); 3) Standard diet+OP (week 8-16); 4) HFHC diet+saline; 5) HFHC diet+OP (week 1-16)—preventive therapy; and 6) HFHC diet+OP (week 8-16)—interventional therapy.

(iii) Exaggerated hyperammonemia: One additional rat group that receives an amino acid-rich (AAs) diet to induce hyperammonemia serves as a positive control.

All animals are sacrificed and tissues are collected to investigate the mechanisms that link OTC dysfunction with NASH development and the pharmacological modulation of hyperammonemia.

Primary end point of these experiments is to ascertain the severity of NASH and fibrosis in the various groups studied. For NASH and fibrosis scoring, histological study is performed and the NASH CRN scoring system is used by an experienced hepato-pathologist blinded to the type of treatment received by the animals (TVL; APD). Commonly described variables in NASH are analyzed on Hematoxylin-eosin stained sections: 1) macro/micro vesicular steatosis, 2) lobular inflammation, 3) hepatocellular ballooning, and 4) apoptotic bodies. Fibrosis/collagen accumulation is assessed using Sirius Red stained sections. In addition, oil red O staining is performed to investigate changes in lipid accumulation and Filipin staining to observe changes in cholesterol.

For secondary end-points: 1) blood samples: analysis of plasma biochemistry (serum ALT, AST, urea, ammonia, albumin, cholesterol-LDL, cholesterol-HDL cholesterol and triglycerides) are performed using Cobas Integra 400 multi analyzer with appropriate kits (Roche Diagnostics, Burgess Hill, West Sussex, UK). 2) Measurement of OTC enzyme activity and assessment of OTC (and other urea cycle related enzymes) is performed using qPCR and Western blot analysis. Changes in OTC localization/zonation are assessed using immunohistochemistry. 3) Pro-fibrogenic, activation-related HSC markers are detected. 4) Pro-inflammatory cytokines/chemokines and macrophage markers are detected. And 5) Apoptosis-related markers are detected.

For power calculations and statistical analysis, experiments are undertaken to demonstrate a significant difference between the different conditions under investigation at a p value of <0.05 with 80% power (using ANOVA with selected post-group comparisons). Previous studies indicate n=12 animals in each group to be sufficient to demonstrate a significant change.

It is expected that (i) animal models of NASH simulating the calorie and fat dense Western diet have hyperammonemia and reduced OTC expression and function; and (2) treatment with an ammonia-reducing agent (for example OP) reduces biochemical, inflammatory and histological indices of liver injury and reverses OTC dysfunction and hyperammonemia.

Example 6

Ammonia-Reducing Agent Treats Liver Cancer

In this example, a rat model of fibrosis/HCC is used to determine whether an ammonia-reducing agent OP can reduce the risk of HCC development.

Animals are studied up to at 16 weeks and examined for the development of HCC. Animals (6-8/group) are treated with diethylnitrosamine (DEN)/nitrosomorpholine (NMOR) to induce fibrosis/HCC as previously described (Mohamed et al., Liver International 2015, 35(3):1063-1076). The six animal groups for study are listed in Table 1.

TABLE 1

Animal groups

1. Sham + saline
2. Sham + OP (week 1-14) - prevention
3. Sham + OP (week 7-14) - treatment
4. DEN + saline
5. DEN + OP (week 1-14) - prevention
6. DEN + OP (week 7-14) - treatment Example 7

Reduction in Ammonia Level Reduces Progression of NAFLD

NAFLD is induced in rats by feeding male rats with a liquid high-fat diet (HFD) (71% of kcal fat) for up to 16 weeks. Obese Zucker rats, which is one of the most commonly used models of NAFLD in rats, are provided. Ornithine in combination with at least one of phenylacetate and phenylbutyrate, for example OP, are administered to the HFD rats and the obese Zucker rats. It is expected that the administration of ornithine in combination with at least one of phenylacetate and phenylbutyrate, which reduces ammonia concentration in the HFD rats and the obese Zucker rats, is effective in reducing progression of NAFLD in diet-induced NAFLD rat models as well as in genetic rat model of NAFLD.

Example 8

Hyperammonemia Worsens Progression of NAFLD and Fibrosis

NAFLD is induced in rats by feeding male rats with a liquid high-fat diet (HFD) (71% of kcal fat) for three weeks. Obese Zucker rats, which is one of the most commonly used models of NAFLD in rats, are provided. Spontaneous hyperammonemia is engineered in both diet-induced and genetic NAFLD rat models by making the rats deficient in ornithine transcarbamoylase (OTC deficiency). OTC deficient rats are made by mutating or deleting the OTC gene in the rats. Induced hyperammonemia is engineered in both diet-induced and genetic NAFLD rat models by feeding high-protein diet to the rats. It is expected that both of the spontaneous and induced hyperammonemia worsen the progression of
NAFLD and fibrosis.

Example 9

Weight Reduction Reduces Progression of NAFLD

NAFLD is induced in rats by feeding male rats with a liquid high-fat diet (HFD) (71% of kcal fat) for three weeks. Obese Zucker rats, which is one of the most commonly used models of NAFLD in rats, are provided. Weight reduction surgery is performed on the HFD rats and the obese. It is expected that the weight reduction surgery reduces progression of NAFLD in diet-induced NAFLD rat models as well as in genetic rat model of NAFLD. It is also expected that the weight reduction improves hepatic nitrogen handling, OTC gene/protein expression and function in the NAFLD rat models.

Although the present disclosure has been described with reference to embodiments and examples, it should be understood that numerous and various modifications can be made without departing from the spirit of the present disclosure. Accordingly, the present disclosure is limited only by the following claims.

All references cited herein, including patents, patent applications, papers, text books, and the like, and the references cited herein, to the extent that they are not already, are hereby incorporated by reference in their entirety. In the event that one or more of the incorporated literature and similar materials differ from or contradict this application, including but not limited to defined terms, term usage, described techniques, or the like, this application controls.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein, including patents, patent applications, papers, text books, and the like, and the references cited herein, to the extent that they are not already, are hereby incorporated by reference in their entirety. In the event that one or more of the incorporated literature and similar materials differ from or contradict this application, including but not limited to defined terms, term usage, described techniques, or the like, this application controls.

What is claimed is:

1. A method of treating or delaying the onset or progression of a disease associated with hepatic stellate cell (HSC) activation, comprising administering an ammonia-lowering agent to a subject in need thereof, wherein the disease associated with HSC activation is non-alcoholic fatty liver disease (NAFLD), liver cancer, or fibrotic condition.

2. The method of claim 1, wherein the disease associated with HSC activation is non-alcoholic fatty liver disease (NAFLD).

3. The method of claim 2, wherein the NAFLD is non-alcoholic steatohepatitis (NASH).

4. The method of claim 2, wherein the NAFLD is steatosis.

5. The method of claim 1, wherein the disease associated with HSC activation is liver cancer.

6. The method of claim 1, wherein the disease associated with HSC activation is a fibrotic condition.

7. The method of claim 6, wherein the fibrotic condition is liver fibrosis.

8. The method of claim 1, wherein the ammonia-lowering agent comprises a magnesium phosphate product (MGP), glycerol phenylbutyrate (GPB), sodium phenylacetate, sodium phenylbutyrate (NaPBA), glutamine, sodium benzoate, L-arabinose, a laxative, an antibiotic, ornithine in combination with at least one of phenylacetate and phenylbutyrate, or any combination thereof.

9. The method of claim 8, wherein the ammonia-lowering agent comprises ornithine in combination with at least one of phenylacetate and phenylbutyrate.

10. The method of claim 9, wherein separate pharmaceutically acceptable salts of the ornithine and at least one of phenylacetate and phenylbutyrate are administered to the subject.

11. The method of claim 10, wherein at least one of phenylacetate and phenylbutyrate is administered as a sodium phenylacetate or sodium phenylbutyrate.

12. The method of claim 9, wherein the ornithine is administered as a free monomeric amino acid or physiologically acceptable salt thereof.

13. The method of claim 9, wherein the ornithine and phenylacetate is administered as ornithine phenylacetate.

14. The method of claim 1, wherein the administration is oral, intravenous, intraperitoneal, intragastric, or intravascular administration.

15. The method of claim 14, wherein the administration is intravenous administration.

16. The method of claim 14, wherein the administration is oral administration.

* * * * *